(12) United States Patent
Little et al.

(10) Patent No.: US 7,285,422 B1
(45) Date of Patent: Oct. 23, 2007

(54) SYSTEMS AND METHODS FOR PREPARING AND ANALYZING LOW VOLUME ANALYTE ARRAY ELEMENTS

(75) Inventors: Daniel P. Little, Patton, PA (US); Maryanne J. O'Donnell-Maloney, Marblehead, MA (US); Charles R. Cantor, Boston, MA (US); Hubert Köster, Concord, MA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 08/786,988

(22) Filed: Jan. 23, 1997

(51) Int. Cl.
*G01N 1/10* (2006.01)

(52) U.S. Cl. .................. 436/180; 436/54; 436/173; 436/174

(58) Field of Classification Search .................. 436/43, 436/49, 54, 164, 165, 166, 171, 174, 179, 436/180, 807, 809, 173, 86; 422/63, 65, 422/68.1, 81, 82.05, 100; 222/420
See application file for complete search history.

(56) References Cited

U.S. PATENT DOCUMENTS

| | | | |
|---|---|---|---|
| 3,568,735 A | 6/1968 | Lancaster | 141/238 |
| 3,776,700 A * | 12/1973 | Gallant | 422/65 |
| 3,807,235 A | 4/1974 | Lefkovitz | 73/863.32 |
| 3,999,689 A | 12/1976 | Ciantro et al. | 222/108 |
| 4,461,328 A | 7/1984 | Kenney | 422/100 |
| 4,548,245 A | 10/1985 | Crandell et al. | 141/237 |
| 4,554,839 A * | 11/1985 | Hewett et al. | 73/864.16 |
| 4,725,677 A | 2/1988 | Köster et al. | 536/27 |
| 4,731,335 A * | 3/1988 | Brigati | 436/180 |
| 4,740,692 A | 4/1988 | Yamamoto et al. | 250/282 |
| 4,779,467 A | 10/1988 | Rainin et al. | 73/863.32 |
| 4,798,706 A | 1/1989 | Brigati | 422/102 |
| 4,844,298 A | 7/1989 | Ohoka et al. | 222/58 |
| 4,877,745 A * | 10/1989 | Hayes et al. | 436/166 |
| 4,882,127 A * | 11/1989 | Rosenthal et al. | 422/50 |
| 4,925,629 A * | 5/1990 | Schramm | |

(Continued)

FOREIGN PATENT DOCUMENTS

DE 9617011 4/1996

(Continued)

OTHER PUBLICATIONS

Zhange et al., "Micro-preparation Procedure for High-sensitivity Matrix-assisted Laser Desorption Ionization Mass Spectrometry", JMS, vol. 30, 1768-1771 (Sep. 1995).*

(Continued)

*Primary Examiner*—Yelena G. Gakh
(74) *Attorney, Agent, or Firm*—Grant Anderson LLP; Bruce D. Grant

(57) ABSTRACT

The invention provides methods for dispensing tools that can be employed to generate multi-element arrays of sample material on a substrate surface. The substrates surfaces can be flat or geometrically altered to include wells of receiving material. The tool can dispense a spot of fluid to a substrate surface by spraying the fluid from the pin, contacting the substrate surface or forming a drop that touches against the substrate surface. The tool can form an array of sample material by dispensing sample material in a series of steps, while moving the pin to different locations above the substrate surface to form the sample array. The invention then passes the prepared sample arrays to a plate assembly that disposes the sample arrays for analysis by mass spectrometry. To this end, a mass spectrometer is provided that generates a set of spectra signal which can be understood as indicative of the composition of the sample material under analysis.

34 Claims, 9 Drawing Sheets

U.S. PATENT DOCUMENTS

| | | | |
|---|---|---|---|
| 4,931,400 A | 6/1990 | Jitsukawa | 435/287 |
| 4,948,442 A | 8/1990 | Manns | 156/73.1 |
| 4,952,518 A * | 8/1990 | Johnson et al. | 436/518 |
| 5,000,921 A * | 3/1991 | Hanaway et al. | 422/100 |
| 5,023,187 A | 6/1991 | Koebler et al. | 436/180 |
| 5,045,694 A | 9/1991 | Beavis et al. | 250/287 |
| 5,077,210 A | 12/1991 | Eigler et al. | 435/176 |
| 5,108,703 A * | 4/1992 | Pfost et al. | 422/65 |
| 5,118,605 A | 6/1992 | Urdea | 435/6 |
| 5,143,854 A | 9/1992 | Pirrung et al. | 436/518 |
| 5,171,989 A * | 12/1992 | Williams et al. | 250/288 |
| 5,175,209 A | 12/1992 | Beattie et al. | 525/54.11 |
| 5,195,657 A | 3/1993 | Wells | 222/330 |
| 5,210,412 A | 5/1993 | Levis et al. | 250/288 |
| 5,221,518 A * | 6/1993 | Mills | 422/62 |
| 5,262,128 A * | 11/1993 | Leighton et al. | 422/100 |
| 5,288,644 A | 2/1994 | Beavis et al. | 436/94 |
| 5,312,233 A | 5/1994 | Tanny et al. | 417/316 |
| 5,338,688 A * | 8/1994 | Deeg et al. | 436/180 |
| 5,350,676 A | 9/1994 | Oberhardt et al. | 435/13 |
| 5,399,501 A | 3/1995 | Pope et al. | 436/532 |
| 5,439,649 A * | 8/1995 | Tseung et al. | 422/99 |
| 5,457,041 A | 10/1995 | Ginaven et al. | 435/172.1 |
| 5,498,545 A | 3/1996 | Vestal | 436/47 |
| 5,503,980 A | 4/1996 | Cantor | 435/6 |
| 5,506,348 A | 4/1996 | Pieles | |
| 5,512,295 A | 4/1996 | Kornberg et al. | 424/450 |
| 5,514,548 A | 5/1996 | Krebber et al. | 435/6 |
| 5,547,835 A | 8/1996 | Köster et al. | 435/6 |
| 5,580,434 A | 12/1996 | Robotti et al. | 204/451 |
| 5,580,733 A | 12/1996 | Levis et al. | 435/6 |
| 5,589,136 A * | 12/1996 | Northrup et al. | 422/102 |
| 5,599,500 A * | 2/1997 | Jones | 422/62 |
| 5,601,982 A | 2/1997 | Sargent et al. | 435/6 |
| 5,605,662 A * | 2/1997 | Heller et al. | 422/68.1 |
| 5,605,798 A | 2/1997 | Köster et al. | 435/6 |
| 5,609,907 A | 3/1997 | Natan | 427/2.12 |
| 5,622,824 A | 4/1997 | Köster et al. | 435/6 |
| 5,643,800 A | 7/1997 | Tarantino et al. | 436/518 |
| 5,658,602 A | 8/1997 | Hayes et al. | |
| 5,663,242 A | 9/1997 | Ghosh et al. | 525/329.4 |
| 5,670,322 A * | 9/1997 | Eggers et al. | 435/6 |
| 5,670,381 A | 9/1997 | Jou et al. | 436/518 |
| 5,677,195 A * | 10/1997 | Winkler et al. | 436/518 |
| 5,688,642 A | 11/1997 | Chrisey et al. | 435/6 |
| 5,691,141 A | 11/1997 | Köster et al. | 435/6 |
| 5,700,642 A | 12/1997 | Monforte et al. | 435/6 |
| 5,716,825 A | 2/1998 | Hancock et al. | 435/286.5 |
| 5,742,049 A | 4/1998 | Holle et al. | |
| 5,743,960 A * | 4/1998 | Tisone | 118/683 |
| 5,746,373 A | 5/1998 | Sanada | 239/102.2 |
| 5,756,050 A * | 5/1998 | Ershow et al. | 422/100 |
| 5,757,392 A | 5/1998 | Zhang | 347/14 |
| 5,770,272 A | 6/1998 | Biemann et al. | |
| 5,770,860 A | 6/1998 | Franzen | 250/288 |
| 5,777,324 A | 7/1998 | Hillenkamp | 250/288 |
| 5,807,522 A | 9/1998 | Brown et al. | 422/50 |
| 5,812,272 A | 9/1998 | King et al. | 356/445 |
| 5,828,063 A | 10/1998 | Koster et al. | 250/288 |
| 5,830,655 A | 11/1998 | Monforte et al. | 435/6 |
| 5,854,486 A | 12/1998 | Dreyfus | |
| 5,864,137 A | 1/1999 | Becker et al. | 250/287 |
| 5,869,240 A * | 2/1999 | Patterson | 435/6 |
| 5,869,242 A | 2/1999 | Kamb | 435/6 |
| 5,872,010 A | 2/1999 | Karger et al. | 346/173 |
| 5,885,775 A | 3/1999 | Haff et al. | 435/6 |
| 5,894,063 A | 4/1999 | Hutchens et al. | 436/155 |
| 5,900,481 A | 5/1999 | Lough et al. | 536/55.3 |
| 5,925,520 A | 7/1999 | Tully et al. | 435/6 |
| 5,927,547 A | 7/1999 | Papen et al. | 222/57 |
| 5,955,729 A * | 9/1999 | Nelson et al. | 250/282 |
| 5,965,363 A | 10/1999 | Monforte et al. | 435/6 |
| 5,969,350 A | 10/1999 | Kerley et al. | 250/287 |
| 5,981,185 A | 11/1999 | Matson et al. | 435/6 |
| 5,985,356 A | 11/1999 | Schultz et al. | 427/8 |
| 6,024,925 A | 2/2000 | Little et al. | 422/100 |
| 6,040,193 A | 3/2000 | Winkler et al. | 436/180 |
| 6,051,378 A | 4/2000 | Monforte et al. | 435/6 |
| 6,079,283 A | 6/2000 | Papen et al. | |
| 6,083,762 A | 7/2000 | Papen et al. | |
| 6,090,558 A | 7/2000 | Butler et al. | 435/6 |
| 6,104,028 A | 8/2000 | Hunter et al. | 250/288 |
| 6,110,426 A | 8/2000 | Shalon et al. | 422/68.1 |
| 6,121,048 A | 9/2000 | Zaffaroni et al. | 436/45 |
| 6,136,269 A | 10/2000 | Winkler et al. | 422/61 |
| 6,194,144 B1 | 2/2001 | Köster | 435/6 |
| 6,197,498 B1 | 3/2001 | Köster | 435/6 |
| 6,207,370 B1 | 3/2001 | Little et al. | 435/6 |
| 6,221,601 B1 | 4/2001 | Köster et al. | 435/6 |
| 6,221,605 B1 | 4/2001 | Köster | 435/6 |
| 6,225,061 B1 | 5/2001 | Becker et al. | 435/6 |
| 6,225,450 B1 | 5/2001 | Köster | 536/22.1 |
| 6,235,478 B1 | 5/2001 | Köster | 435/6 |
| 6,238,871 B1 | 5/2001 | Köster | 435/6 |
| 6,258,538 B1 | 7/2001 | Köster et al. | 435/6 |
| 6,265,716 B1 | 7/2001 | Hunter et al. | 250/288 |
| 6,268,131 B1 | 7/2001 | Kang et al. | 435/6 |
| 6,268,144 B1 | 7/2001 | Köster | 435/6 |
| 6,277,573 B1 | 8/2001 | Köster | 435/6 |
| 6,287,872 B1 | 9/2001 | Schurenberg et al. | |
| 6,300,076 B1 | 10/2001 | Köster | 435/6 |
| 6,303,309 B1 | 10/2001 | Jurinke et al. | 435/6 |
| 6,322,970 B1 | 11/2001 | Little et al. | 435/6 |
| 6,342,396 B1 | 1/2002 | Perrin et al. | 436/518 |
| 6,387,628 B1 | 5/2002 | Little et al. | 435/6 |
| 6,428,955 B1 | 8/2002 | Köster et al. | 435/6 |
| 6,485,913 B1 | 11/2002 | Becker et al. | 435/6 |
| 6,500,621 B2 | 12/2002 | Köster | 435/6 |
| 6,558,902 B1 | 5/2003 | Hillenkamp | 435/6 |
| 6,566,055 B1 | 5/2003 | Monforte et al. | 435/6 |
| 6,569,385 B1 | 5/2003 | Little et al. | 422/100 |
| 6,589,485 B2 | 7/2003 | Köster | 422/104 |
| 6,602,662 B1 | 8/2003 | Köster et al. | 435/6 |
| 6,635,452 B1 | 10/2003 | Monforte et al. | 435/91.1 |
| 6,670,609 B2 | 12/2003 | Franzen et al. | |
| 2001/0008615 A1 | 7/2001 | Little et al. | |
| 2001/0055811 A1 | 12/2001 | Hillenkamp | |
| 2002/0009394 A1 | 1/2002 | Koster et al. | |
| 2002/0018999 A1 | 2/2002 | Henriksson et al. | |
| 2002/0040130 A1 | 4/2002 | Braun | |
| 2002/0102725 A1 | 8/2002 | Zabarovsky et al. | |
| 2002/0109085 A1 | 8/2002 | Hillenkamp et al. | |
| 2002/0142483 A1 | 10/2002 | Yao et al. | |
| 2002/0155587 A1 | 10/2002 | Opalsky et al. | |
| 2003/0003465 A1 | 1/2003 | Little et al. | |
| 2003/0017469 A1 | 1/2003 | Risinger et al. | |
| 2003/0022225 A1 | 1/2003 | Monforte et al. | |
| 2003/0033091 A1 | 2/2003 | Opalsky et al. | |
| 2003/0036057 A1 | 2/2003 | Braun et al. | |
| 2003/0096426 A1 | 5/2003 | Little et al. | |
| 2003/0111494 A1 | 6/2003 | Lin et al. | |
| 2003/0113233 A1 | 6/2003 | Nanthakumar | |
| 2003/0113745 A1 | 6/2003 | Monforte et al. | |
| 2003/0124735 A1 | 7/2003 | Nanthakumar et al. | |
| 2003/0129589 A1 | 7/2003 | Koster et al. | |
| 2003/0148528 A1 | 8/2003 | Hillenkamp | |
| 2003/0180148 A1 | 9/2003 | Weng | |
| 2003/0180749 A1 | 9/2003 | Koster et al. | |
| 2003/0190644 A1 | 10/2003 | Braun et al. | |
| 2003/0207297 A1 | 11/2003 | Koster et al. | |
| 2003/0220844 A1 | 11/2003 | Manellos et al. | |
| 2003/0224418 A1 | 12/2003 | Braun et al. | |

| | | |
|---|---|---|
| 2003/0228594 A1 | 12/2003 | Koster et al. |

FOREIGN PATENT DOCUMENTS

| | | |
|---|---|---|
| DE | 9618032 | 5/1996 |
| DE | 9628178 | 7/1996 |
| DE | 9754978 | 12/1997 |
| DE | 19731479 | 8/1998 |
| DE | 19731479 A1 | 8/1998 |
| EP | 0268237 B1 | 11/1987 |
| EP | 0268237 B1 | 5/1988 |
| EP | 0339781 | 11/1989 |
| EP | 0396116 | 11/1990 |
| EP | 0500506 | 8/1992 |
| EP | 0543550 | 5/1993 |
| EP | 0543550 A1 | 5/1993 |
| EP | 1164203 | 12/2001 |
| EP | 1262564 | 12/2002 |
| EP | 1271609 | 1/2003 |
| GB | 2017105 | 3/1979 |
| GB | 2233654 A | 1/1991 |
| GB | 2312782 | 11/1997 |
| GB | 2332273 | 6/1999 |
| JP | 2215399 | 8/1990 |
| JP | A-8-233710 | 9/1996 |
| JP | 8290377 | 11/1996 |
| WO | 8402579 | 7/1984 |
| WO | 8805074 | 7/1988 |
| WO | 8805074 A1 | 7/1988 |
| WO | 8409406 | 10/1989 |
| WO | 8911270 | 11/1989 |
| WO | WO89/10786 | 11/1989 |
| WO | 8912694 | 12/1989 |
| WO | WO 1989/12624 | 12/1989 |
| WO | 9001564 | 2/1990 |
| WO | 9207879 | 5/1992 |
| WO | 9213629 | 8/1992 |
| WO | 9309668 | 5/1993 |
| WO | 9314108 | 7/1993 |
| WO | 9314108 A1 | 7/1993 |
| WO | 9403774 | 2/1994 |
| WO | 9403774 A1 | 2/1994 |
| WO | 9411530 | 5/1994 |
| WO | 9411735 | 5/1994 |
| WO | WO/94/11529 | 5/1994 |
| WO | 9416101 | 7/1994 |
| WO | 9421822 | 9/1994 |
| WO | 9427719 | 12/1994 |
| WO | 9504524 | 2/1995 |
| WO | 9511755 | 5/1995 |
| WO | 9511755 A1 | 5/1995 |
| WO | 9513538 | 5/1995 |
| WO | 9525116 | 9/1995 |
| WO | 9525175 | 9/1995 |
| WO | WO/95/30773 | 11/1995 |
| WO | 9535505 A1 | 12/1995 |
| WO | WO/96028 36 A1 | 2/1996 |
| WO | 9619587 | 6/1996 |
| WO | 9629431 | 9/1996 |
| WO | 9632504 | 10/1996 |
| WO | 9636731 | 11/1996 |
| WO | 9708306 | 3/1997 |
| WO | 9716699 | 5/1997 |
| WO | 9733000 | 9/1997 |
| WO | 9742348 | 11/1997 |
| WO | 9743617 | 11/1997 |
| WO | 9803257 | 1/1998 |
| WO | 9805965 | 2/1998 |
| WO | 9805965 A1 | 2/1998 |
| WO | 9812355 | 3/1998 |
| WO | 9820166 | 5/1998 |
| WO | 9822541 | 5/1998 |
| WO | 9822541 A2 | 5/1998 |
| WO | 9826179 | 6/1998 |
| WO | 9834116 | 8/1998 |
| WO | 9834116 A1 | 8/1998 |
| WO | 9839481 | 9/1998 |
| WO | 9839481 A1 | 9/1998 |
| WO | WO03087410 | 10/2003 |

OTHER PUBLICATIONS

Znahg et al. "Capillary electrophoresis combined with MALDI-MS spectrometry: continuous deposition on a matrix-precoated membrane target", J. Mass Sectr., 1996, v. 31, No. 9, pp. 1039-1046 (Abstract).*

Nicola et al. "Application of the fast-evaporation sample preparation method for improving quantification of angiotensin II by matrix-assisted laser desorption/ionization", Parif Communications in Mass Spectrometry, 1995, v. 9, pp. 1164-1171.*

Vorm et al. "Improved Resolution and Very High Sensitivity in MALDI TOF of Matrix Surfaces Made by Fast Evaporation", Analytical Chemistry, 1994, v. 66, pp. 3281-3287.*

Arshady, Reza, Beaded polymer supports and gels: I. Manufacturing techniques, *Journal of Chromatography*, 586:181-197 (1991).

Arshady, Reza, Beaded polymer supports and gels: II. Physico-chemical criteria and functionalization, *Journal of Chromatography*, 586:199-219 (1991).

Batsita-Viera et al., A new method for reversible immobilization of thiol biomolecules bsed on solid-phase bound thiolsulfonate groups, *App. Biochem and Biotech*,31:175-195 (1991).

English version of Japanese Patent, JP63230086 A 880926 DW8844, WPI/Derwent, AN88-311964, Carry immobilise physiological active substance comprise bind chain form di sulphide compound epoxy group latex contain polymer article.

English version of Japanese Patent, JP2215399 A 90028 DW9040, WPI/Derwent, AN90-302767, Method detect DNA de single strand combination DNA prime correspond base sequence forming replica.

Hayashi et al., Immobilization of thiol proteases onto porous poly(vinyl alcohol) beads, *Polymer Journal*, 25:5, 489-497(1993).

Manoharan et al., A 2'-O-thiol tether in the ribose moiety of nucleic acids for conjugation chemistry, *Gene*, 149:147-156 (1994).

Pon, et al., Derivation of controlled pore glass beads fo rsolid phase oligonucleotide synthesis, *BioTechniques*, 6:8, 770-775 (1988).

Zukermann et al., Efficient methods for attachment of thiol specific probes to the 3'-ends of synthetic oligodeoxyribonucleotides, *Nucleic Acids Research*, 15:13, 5305-5321 (1987).

"SEQUENOM Signs Agreement With Bruker-Franzen Analytik to Develop Mass Spectrometer for DNA Massarray Analysis", Press Release: Jan. 12, 1998, http://www.sequenom.com/pressrelease.htm.

"SEQUENOM Uses DNA MassArray™ to Sequence Section of Human Cancer-Related p53 Gene", Press Release: Mar. 27, 1998, http://www.sequenom.com/pressrelease.htm.

"SEQUENOM Reports DNA MassArray™ Technology More Sensitive Than Electrophoretic Methods in Detecting Gene Mutations: Automated DNA Analysis System Can Speed Up Microsatellite Analyses", Press Release: Dec. 15, 1997, http://www.sequenom.com/pressrelease.htm.

"SEQUENOM Reports On Use of Its DNA MassArray™ Technology to Analyze Genes Associated with Alzheimer's Disease adn Arteriosclerosis: Technology Has Applications in Drug Development", Press Release: Sep. 22, 1997, http://www.sequenom.com/pressrelease.htm.

"SEQUENOM Advances the Industrial Genomics Revolution with the Launch of Its DNA MassArray™ Automated Process Line", Press Release: Sep. 28, 1998, http://www.sequenom.com/pressrelease.com.

Braun et al., "Improved Analysis of Microsatellites Using Mass Spectrometry", *Genomics 46*:18-23 (1997).

Chrisey et al., Covalent attachment of synthetic DNA to self-assembled monlayer films, *Nucl. Acids Res.* 24:3031-3039 (1996).

Chrisey et al., Fabrication of patterned DNA surfaces, *Nucl. Acids. Res.* 24:3040-3047 (1996).

Church et al., "Multiplex DNA Sequencing", *Science 240*:185-188 (1988).

Crain, "Mass spectrometric techniques in nucleic acid research", *Mass Spectr. Rev.* 9:505-554 (1990).
Database WPI, Derwent Publications #198942, citing International PCT Application No. WO 89/09406 published Oct. 5, 1989.
Database WPI, Derwent Publications #199703, citing Japanese Patent No. 8290377 published Nov. 5, 1996.
Greene and Wuts, *Protective Groups in Organic Synthesis*, 2nd Edition, Wiley & Sons (1991).
Hillenkamp and Ehring, Laser desorption mass spectrometry Part 1: Basic mechanisms and techniques, *Mass Spectrometry in the Biological Sciences: A tutorial*, pp. 165-179 (1992).
Hillenkamp et al., Matrix assisted UV-laser desorption/ionization: A new approach to mass spectrometry of large biomolecules, *Bio mass Spectr.*, Burlingame and McCloskey (eds.), pp. 49-61, Elsevier Science Publishers B.V., Amsterdam (1989).
Jett et al., "High-Speed DNA Sequencing: An Approach Based Upon fluorescence Detection of Single Molecules", *J. Bio Strut & Dynam.* 7(2):301-09 (1989).
Köster et al., N-acyl protecting groups for deoxynucleotides: A quantitative and comparative study, *Tetrahedron* 37:363-369 (1981).
Köster et al., Oligonucleotide synthesis and multiplex DNA sequencing using chemiluminescent detection, *Nucl. Acids Res., Symposium Series No.* 24:318-321, (1991).
Köster et al., "Well-Defined Insoluble Primers for the Enzymatic Synthesis of Oligo- and Polynucleotides", *Hoppe-Seyler's Z. Physiol. Chem.* 359:1579-1589 (1978).
Köster et al., "A strategy for rapid and efficient DNA sequencing by mass spectrometry", *Nature Bio* 14:1123-1128 (1996).
Landegren et al., "DNA Diagnostics—Molecular techniques and automation", *Science* 242:229-237 (1988).
Li et al., "Analysis of single mammalian cell lysates by mass spectrometry", *J. Am. Chem. Soc.* 118:11662-11663 (1996).
Li et al., "High-Resolution MALDI Fourier Transform Mass Spectrometry of Oligonucleotides", *Anal Chem* 68(13):2090-2096 (1996).
Little et al., "Mass spectrometry from miniaturized arrays for full comparative DNA analysis", *Nature Med* 3(12):1413-1416 (1997).
Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet", *Anal chem* 69:4540-4546 (1997).
Little et al., "Direct detection of synthetic and biologically generated double-stranded DNA by MALDI-TOF MS", *J. Mass Spec* 17:1-8 (1997).
Martin, "New technologies for large-genome sequencing", *Genome* 31:1073-1080 (1989).
McCray and Trentham, "Properties and uses of photoreactive caged compounds", *Annu. Rev. Biophys. Biophys. Chem.* 18:239-270 (1989).
Moini et al., "A moving belt device to couple high-performance liquid chromatography and chemical reaction interface mass spectrometry", *Bio Mass Spect* 20:308-312 (1991).
Nelson et al., "Volatilization of high molecular weight DNA by pulsed laser ablation of frozen aqueous solutions", *Science* 246:1585-1587 (1989).
Nelson et al., Time-of-flight mass spectrometry of nucleic acids by laser ablation and ionization from a frozen aqueous matrix, *Rapid Communications in Mass Spectrometry* 4:348-351 (1990).
Nordhoff et al., "Ion stability of nucleic acids in infrared matrix-assisted laser desorption/ionization mass spectrometry", *Nuc Acids Res.* 21(15):3347-3357 (1993).
Nordhoff et al., "Matrix-assisted laser desorption/ionization mass spectrometry of nucleic acids with wavelenght in the ultraviolet and infrared", *Rapid Comm. Mass Spectrom.* 6:771-776 (1992).
O'Donnell et al., "MassArray as an enabling technology for the industrial-scale analysis of DNA", *Genetic Engineering News* 17(21) (1997).
O'Donnell et al., "High-Density, Covalent Attachment of DNA to Siliocn Wafers for Analysis by MALDI-TOF Mass Spectrometry", *Analytical Chemistry* 69(13):2438-2443 (1997).

O'Donnell-Maloney et al., "Microfabrication and array technologies for DNA sequencing and diagnostics", *Genetic Analysis: Biomolecular Engineering* 13:151-157 (1996).
Overberg et al., "Laser desorption mass spectrometry: part II performance and applications of matrix-assisted laser desorption/ionization of large biomolecules", *Mass Spect in the Biolog Science: A Tutorial* 181-197 (1992).
Rolfs et al., *PCR: Clinical Diagnostics and Research*, Springer-Verlag (1994).
Ruppert et al., "Preparation of plasmid DNA as Sequencing Templates in a Microtiter Plate Format", Paper presented, Cold Spring Harbor Laboratory.
Ruppert et al., "A rapid and high throughput method for plasmid isolations", Presented: Automation in Mapping and DNA Sequencing Conference, Aug. 31-Sep. 2, 1994.
Schram, Karl H., "Mass spectrometry of nucleic acid components", *Bio Appl of Mass Spect.* 34:203-287 (1990).
Shaler et al., "Effect of Impurities on the matrix-Assisted Laser Desorption Mass Spectra of Single-Stranded Oligodeoxynucleotides", *Anal. Chem.* 68:576-579 (1996).
Siuzdak, Gary, "The emergence of mass spectrometry in biochemical research", *Proc. natl. Acad. Sci. USA* 91:11290-11297 (1994).
Smith R. D., "New developments in biochemical mass spectrometry: Electrospray Ionization", *Anal. Chem.* 62:882-899 (1990).
Smith, Cassandra L., "cDNA Fingerprinting of Breast Cancer Tumor Cells", Boston Univ., MA (1996).
Tang et al., "Matrix-assisted laser desorption/ionization mass spectrometry of immobilized duplex DNA probes", *Nucleic Acids Research* 23:3126-3131 (1995).
Tomer et al., "Coaxial Continuous Flow Fast Atom Bombardment for Higher-Molecular-Weight Peptides: Comparison with Static Fast Atom Bombardment and electrospray Ionization", *Bio Mass Spect* 20:783-788 (1991).
Trainor, "DNA Sequencing, Automation, and the Human Genome", *Anal. Chem.* 62:418-426 (1990).
Valaskovic et al., "Attomole protein characterization by capillary electrophoresis-mass spectrometry", *Science* 273:1199-1202 (1996).
Williams, Time of flight mass spectrometry of DNA laser-ablated from frozen aqueous solutions: applications to the Human Genome Project, *Intl. J. Mass Spectrom. and Ion Processes* 131:335-344 (1994).
Wu et al., "Matrix-assisted Laser Desorption Time-of-flight Mass Spectrometry of Oligonucleotides Using 3-Hydroxypicolinic Acid as an Ultraviolet-sensitive Matrix", *Rapid Comm Mass Spec* 7:142-146 (1993).
Wu et al., "Time-of-Flight Mass Spectrometry of Underivatized Single-Stranded DNA Oligomers by Matrix-Assisted Laser Desorption", *Anal. Chem.* 66:1637-1645 (1994).
O'Donnell-Maloney et al., "The development of microfabricated arrays for DNA sequencing and analysis" *TIBTECH* 14:401-407 (1996).
Database WPI, WPI Acc. No. 98-348616/199830, citing International PCT Application No. WO 98/26179 published Jun. 18, 1998.
Stults and Marsters, "Improved electrospray ionization of synthetic oligodeoxynucleotides", *Rapid Comm. Mass Spectrom.* 5:359-363 (1991).
Microdrop Gmbh, Norderstedt, Germany, Autodrop system.
Lee, et al., Direct Measurement of the Forces Between Complementary Strands of DNA, Science, vol. 266, Nov. 4, 1994, 771-773.
Vorm, et al, Improved Mass Accuracy in Matrix-Assisted Laser Desorption/Ionization Time-Of-Flight Mass Spectrometry of Peptides. Journal of The American Society For Mass Spectrometry, Nov. 1994, V5(N11): 955-958.
Schober, et al., Accurate High-Speed Liquid Handling of Very Small Biological Samples, Biotechniques, (1993) 15(2):324-329.
Asseline et al. "New Solid-Phase For Automated Synthesis of Oligonucleotides Containing An Amino-Alkyl Linker at Their 3'-End," *Tetrahedron Letters* 31(1): 81-84 (1990).
Beattie et al. "123:112593k Synthesis and use of oligonucleotide libraries," *Chemical Abstracts* 123: 1172 (1995).

Bonfils, E. and N.T. Thuong. "Solid Phase Synthesis of 5', 3'-Bifunctional Oligodeoxyribonucleotides Bearing a Masked Thiol Group at the 3'-End," *Tetrahedron Letters* 32(26): 3053-3056 (1991).

Day et al. "Immobilization of polynucleotides on magnetic particles," *Biochem. J.* 278: 735-740 (1991).

Debitsudo, A. "121:109581h Preparation of oligonucleotide monolayer," *Chemical Abstracts 121*: 1163:1163 (1994).

Debitsudo, A. "121:83891g Preparation of nucleotide thioalkyl esters and monomolecular membrane," *Chemical Abstracts 121*: 1166 (1994).

Debitsudo, A. "122:291447q Organic super-thin fim of oligonucleotide derivative and method for its preparation," *Chemical Abstracts 122*: 1100 (1995).

Derwent No. 011716230, WPI Acc. No. 1998-133140/199813 for PCT Patent Application WO9805965 A1, "Identification of characteristics of eukaryotic cells -after covalent immobilisation on solid support,".

Derwent No. 011999582, WPI Acc. No. 1998-416492/199836 for PCT Patent Application WO9834116 A1, "Isolation and determination of analyte -by capture on specific binding particles and concentration of these on second, limited binding surface before detection, used e.g. for detecting RNA,".

Derwent No. 012012061, WPI Acc. No. 1998-428971/199837 for German Patent Application DE19731479 A, "Device for analysis of target chemicals has light emitting array—with chemical binder elements attached to array to capture target chemicals which change emitted light pattern accordingly,".

Emmett, M.R. and R.M. Caprioli. "Micro-Electrospray Mass Spectrometry: Ultra-High-Sensitivity Analysis of Peptides and Proteins," *J. Am. Soc. Mass Spectrometry* 5: 605-613 (1994).

Hofstadler et al. "Capillary Electrophoresis—Electrospray Ionization Fourier Transform Ion Cyclotron Resonance Mass Spectrometry for Direct Analysis of Cellular Proteins," *Anal. Chem.* 67: 1477-1480 (1995).

Jespersen et al. "Attomole Detection of Proteins by Matrix-assisted Laser Desorption/Ionization Mass Spectrometry with the Use of Picolitre Vials," *Rapid Communications in Mass Spectrometry* 8(8): 581-584 (1994).

Li et al. "Analysis of Single Mammalain Cell Lysates by Mass Spectrometry," *J. Am. Chem. Soc. 118*: 11662-11663 (1996).

Lyttle, M.H. "126:235533k Versatile Linker Chemistry for Synthesis of 3'-Modified DNA," *Chemical Abstracts 126*(18): 314 (1997).

Solouki et al. "Attomole Biomolecule Mass Analysis by MAtrix-Assisted Laser Desorption/Ionization Fourier Transform Ion Cyclotron Resonance," *Anal. Chem.* 67:4139-4144 (1995).

Wilm et al. "Electrospray and Taylor-Cone theory, Dole's beam of macromolecules at last," *International Journal of Mass Spectrometry and Ion Processes 136*: 167-180 (1994).

Valaskovic et al. "Attomole Protein Characterization by Capillary Electrophoresis- Mass Spectrometry," *Science 273*: 1199-1202 (1996).

Valaskovic et al. "Attomole-Sensitivity Electrospray Source for Large-Molecule Mass Spectrometry," *Anal. Chem.* 67: 3802-3805 (1995).

Wahl et al. "Use of small-diameter capillaries for increasing peptide and protein detection sensitivity in capillary electrophoresis-mass spectrometry," *Electrophoresis 14*: 448-457 (1993).

Zhang et al. "Micro-preparation Procedure for High-sensitivity Matrix-assisted Laser Desorption Ionization Mass Spectrometry," *Journal of Mass Spectrometry 30*: 1768-1771 (1995).

Certified English language translation of WO98/03257, "Solid supports for analytical measurement methods, their production and their use," cited at Item AJ.

Derwent # 011716230, WPI Acc No. 1998/199813, for PCT Patent Application WO 9805965 A, "Identification of characteristics of eukaryotic cells—after covalent immobilisation on solid support," cited at Item AK.

Derwent #012012061, WPI Acc. No. 1998-428971/199837, for German Application No. DE 19731479 A1, "Device for analysis of target chemicals has light emitting array—with chemical binder elements attached to array to capture target chemicals which change emitted light pattern accordingly," cited at Item AB.

Derwent #002061834, WPI Acc. No. 90-302767, for Japanese Application No. JP 2215399, "Method for detecting DNA—includes de-naturing to single strand, combining with DNA primer having corresp. base sequence forming replicator etc," cited at Item AC.

Manoharan et al., "A 2'-O-thiol Tether in the Ribose Moiety of Nucleic Acids for Conjugation Chemistry", *Gene*, 149:147-156 (1994).

O'Donnel-Maloney et al., "Microfabrication and Array Technologies for DNA Sequencing and Diagnostics", *Genetic Analysis Biomolecular Engineering*, 13:161-157 (1996).

Pon et al., "Derivatization of Controlled Pore Glass Beads for Solid Phase Oligonucleotide Synthesis", *BioTechnique*, 6(8):768-770, 773-775 (1988).

Brummel et al., "Evaluation of mass spectrometric methods applicable to the direct analysis of non-peptide bead-bound combinatorial libraries",*Anal. Chem.*, 68:237-242 (1996).

Dai, Yuqin, et al., Two-Layer Sample Preparation: A Method for MALDI-MS Analysis of Complex Peptide and Protein Mixtures, Analytical. Chemistry, (1999), 1087-1097, 71(5), American Chemical Society.

Nicola, Anthony J., et al., Application of the Fast-evaporation Sample Preparation Method for Improving Quantification of Angiotensin II by Matrix-assisted Laser Desorption/Ionization, Rapid Communications in Mass Spectrometry, (1995), 1184-1171, 9, John Wiley & Sons, Ltd.

Vorm, Ole, et al., Improved Resolution and Very High Sensitivity in MALDI TOF of Matrix Surfaces Made by Fast Evaporation, Analytical Chemistry, (1994), 3281-3287, 56(19), American Chemical Society.

Vorm, Ole, et al, Improved Mass Accuracy In Matrix-Assisted Laser Desorption/Ionization Time-of-Flight Mass Spectrometry of Peptides, J. Am. Soc. Mass Spectrom, (1994), 955-958, 5, American Society for Mass Spectrometry.

Fast Evaporation, http address www.chemistry.wustl.edu/~msf/damon/samp_prep_fast_evap.html, pp. 1-Z, Sample Preparation—Fast Evaporation.

Sample Preparation—References, pp. 1-3 http address www.chemistry.wustl.edu/~mef/damon/samp_prep_references.html.

On-Probe Decontamination for MALDI Samples, pp. 1-2, http address www.chemistry.msu.edu/faculty/bruening/onprobepurification.htm, Matrix.

M.C. Fitzgerald et al., "The promise of matrix-assisted laser desorption-ionization (MALDI) mass spectrometry," Annu. Rev. Biophys. Biomol. Struct. 24: 117-140 (1995).

Kozal et al., "Extensive Polymorphisms Observed in HIV-1 Clade B Protease Gene Using High-Density Oligonucleotide Arrays," Nature Medicine, vol. 2, No. 7, pp. 753-759, (1996).

Wallace, "Ink-Jet Based Fluid Microdispensing in Biochemical Applications," Microfab Technologies Inc., Laboratory Automation News, vol. 1, No., 5 pp. 6-9, (1996).

* cited by examiner

| k1 6968 Da 170 RP | k2 6968 Da 100 RP | k3 6988 Da 90 RP | k4 6977 Da 100 RP | k5 6971 Da 170 RP | k6 6968 Da 110 RP | k7 6972 Da 160 RP | k8 6978 Da 110 RP | k9 6952 Da 250 RP | k10 6965 Da 300 RP |
|---|---|---|---|---|---|---|---|---|---|
| l1 6965 Da 130 RP | l2 6989 Da 140 RP | l3 6982 Da 210 RP | l4 6996 Da 50 RP | l5 6982 Da 160 RP | l6 6968 Da 180 RP | l7 6984 Da 130 RP | l8 6968 Da 200 RP | l9 6996 Da 80 RP | l10 6968 Da 100 RP |
| m1 6966 Da 190 RP | m2 6979 Da 120 RP | m3 6975 Da 120 RP | m4 6968 Da 190 RP | m5 6976 Da 110 RP | m6 6986 Da 120 RP | m7 6973 Da 160 RP | m8 6978 Da 160 RP | m9 6975 Da 230 RP | m10 6955 Da 250 RP |
| n1 6961 Da 340 RP | n2 6971 Da 180 RP | n3 6970 Da 150 RP | n4 6960 Da 300 RP | n5 6985 Da 120 RP | n6 6953 Da 210 RP | n7 6971 Da 140 RP | n8 6962 Da 160 RP | n9 6957 Da 150 RP | n10 6960 Da 160 RP |
| o1 6965 Da 140 RP | o2 6960 Da 230 RP | o3 6976 Da 200 RP | o4 6953 Da 250 RP | o5 6983 Da 110 RP | o6 6967 Da 250 RP | o7 6970 Da 150 RP | o8 6973 Da 70 RP | o9 6953 Da 140 RP | o10 6952 Da 140 RP |
| p1 6976 Da 140 RP | p2 6981 Da 90 RP | p3 6972 Da 180 RP | p4 6969 Da 90 RP | p5 6984 Da 130 RP | p6 6968 Da 100 RP | p7 6958 Da 290 RP | p8 6981 Da 100 RP | p9 6978 Da 110 RP | p10 6965 Da 150 RP |
| q1 6976 Da 170 RP | q2 6985 Da 100 RP | q3 6990 Da 120 RP | q4 6989 Da 90 RP | q5 6984 Da 90 RP | q6 6969 Da 170 RP | q7 6979 Da 70 RP | q8 6968 Da 140 RP | q9 6973 Da 120 RP | q10 6950 Da 120 RP |
| r1 6966 Da 130 RP | r2 6960 Da 150 RP | r3 6969 Da 100 RP | r4 6964 Da 180 RP | r5 6966 Da 130 RP | r6 6970 Da 110 RP | r7 6972 Da 90 RP | r8 6939 Da 130 RP | r9 6951 Da 230 RP | r10 6965 Da 200 RP |
| s1 6963 Da 130 RP | s2 6953 Da 210 RP | s3 6970 Da 120 RP | s4 6971 Da 170 RP | s5 6957 Da 130 RP | s6 6956 Da 160 RP | s7 6966 Da 140 RP | s8 6975 Da 120 RP | s9 6951 Da 230 RP | s10 6969 Da 120 RP |
| t1 6974 Da 90 RP | t2 6958 Da 160 RP | t3 6959 Da 120 RP | t4 6952 Da 100 RP | t5 6959 Da 110 RP | t6 6954 Da 100 RP | t7 6950 Da 160 RP | t8 6974 Da 140 RP | t9 6967 Da 150 RP | t10 6950 Da 230 RP |

LASER POWER = 41000 FOR ALL SPECTRA.
EACH SPECTRUM THE SUM OF 10-30 SINGLE SHOTS.

FIG. 9

SYSTEMS AND METHODS FOR PREPARING AND ANALYZING LOW VOLUME ANALYTE ARRAY ELEMENTS

FIELD OF THE INVENTION

The invention relates to systems and methods for preparing a sample for analysis, and more specifically to systems and methods for dispensing low volumes of fluid material onto a substrate surface for generating an array of samples for diagnostic analysis.

BACKGROUND OF THE INVENTION

In recent years, developments in the field of the life sciences have proceeded at a breathtaking rate. Universities, hospitals and newly formed companies have made groundbreaking scientific discoveries and advances that promise to reshape the fields of medicine, agriculture, and environmental science. However, the success of these efforts depends, in part, on the development of sophisticated laboratory tools that will automate and expedite the testing and analysis of biological samples. Only upon the development of such tools can the benefits of these recent scientific discoveries be achieved fully.

At the forefront of these efforts to develop better analytical tools is a push to expedite the analysis of complex biochemical structures. This is particularly true for human genomic DNA, which is comprised of at least about one hundred thousand genes located on twenty four chromosomes. Each gene codes for a specific protein, which fulfills a specific biochemical function within a living cell. Changes in a DNA sequence are known as mutations and can result in proteins with altered or in some cases even lost biochemical activities; this in turn can cause a genetic disease. More than 3,000 genetic diseases are currently known. In addition, growing evidence indicates that certain DNA sequences may predispose an individual to any of a number of genetic diseases, such as diabetes, arteriosclerosis, obesity, certain autoimmune diseases and cancer. Accordingly, the analysis of DNA is a difficult but worthy pursuit that promises to yield information fundamental to the treatment of many life threatening diseases.

Unfortunately, the analysis of DNA is made particularly cumbersome due to size and the fact that genomic DNA includes both coding and non-coding sequences (e.g., exons and introns). As such, traditional techniques for analyzing chemical structures, such as the manual pipeting of source material to create samples for analysis, are of little value. To address the scale of the necessary analysis, scientist have developed parallel processing protocols for DNA diagnostics.

For example, scientist have developed robotic devices that eliminate the need for manual pipeting and spotting by providing a robotic arm that carries at its proximal end a pin tool device that consists of a matrix of pin elements. The individual pins of the matrix are spaced apart from each other to allow each pin be dipped within a well of a microtiter plate. The robotic arm dips the pins into the wells of the microtiter plate thereby wetting each of the pin elements with sample material. The robotic arm then moves the pin tool device to a position above a target surface and lowers the pin tool to the surface contacting the pins against the target to form a matrix of spots thereon. Accordingly, the pin tool expedites the production of samples by dispensing sample material in parallel.

Although this pin tool technique works well to expedite the production of sample arrays, it suffers from several drawbacks. First, during the spotting operation, the pin tool actually contacts the surface of the substrate. Given that each pin tool requires a fine point in order that a small spot size is printed onto the target, the continuous contact of the pin tool against the target surface will wear and deform the fine and delicate points of the pin tool. This leads to errors which reduce accuracy and productivity.

An alternative technique developed by scientists employs chemical attachment of sample material to the substrate surface. In one particular process, DNA is synthesized in situ on a substrate surface to produce a set of spatially distinct and diverse chemical products. Such techniques are essentially photolithographic in that they combine solid phase chemistry, photolabile protecting groups and photo activated lithography. Although these systems work well to generate arrays of sample material, they are chemically intensive, time consuming, and expensive.

It is further troubling that neither of the above techniques provide sufficient control over the volume of sample material that is dispensed onto the surface of the substrate. Consequently, error can arise from the failure of these techniques to provide sample arrays with well controlled and accurately reproduced sample volumes. In an attempt to circumvent this problem, the preparation process will often dispense generous amounts of reagent materials. Although this can ensure sufficient sample volumes, it is wasteful of sample materials, which are often expensive and of limited availability.

Even after the samples are prepared, scientist still must confront the need for sophisticated diagnostic methods to analyze the prepared samples. To this end, scientists employ several techniques for identifying materials such as DNA. For example, nucleic acid sequences can be identified by hybridization with a probe which is complementary to the sequence to be identified. Typically, the nucleic acid fragment is labeled with a sensitive reporter function that can be radioactive, fluorescent, or chemiluminescent Although these techniques can work well, they do suffer from certain drawbacks. Radioactive labels can be hazardous and the signals they produce decay over time. Non-isotopic (e.g. fluorescent) labels suffer from a lack of sensitivity and fading of the signal when high intensity lasers are employed during the identification process. In addition, labeling is a laborious and time consuming error prone procedure.

Consequently, the process of preparing and analyzing arrays of a biochemical sample material is complex and error prone.

SUMMARY OF THE INVENTION

Accordingly, it an object of the invention to provide improved systems and methods for preparing arrays of sample material.

It is a further object of the invention to provide systems that allow for the rapid production of sample arrays.

It is yet another object of the invention to provide systems and methods for preparing arrays of sample material that are less expensive to employ and that conserve reagent materials.

It is a further object of the invention to provide systems and methods for preparing arrays of sample material that provide high reproducibility of the arrays generated.

Other objects of the invention will in part be obvious and in part be disclosed in the following.

The invention provides, in one aspect, serial and parallel dispensing tools that can be employed to generate multi-element arrays of sample material on a substrate surface. The substrates surfaces can be flat or geometrically altered to include wells of receiving material. In one embodiment, the invention provides a tool that allows the parallel development of a sample array. To this end, the tool can be understood as an assembly of vesicle elements, or pins, wherein each of the pins can include a narrow interior chamber suitable for holding nano liter volumes of fluid. Each of the pins can fit inside a housing that itself has an interior chamber. The interior housing can be connected to a pressure source that will control the pressure within the interior housing chamber to regulate the flow of fluid through the interior chamber of the pins. This allows for the controlled dispensing of defined volumes of fluid from the vesicles. In an alternative embodiment, the invention provides a tool that includes a jet assembly that can include a capillary pin having an interior chamber, and a transducer element mounted to the pin and capable of driving fluid through the interior chamber of the pin to eject fluid from the pin. In this way, the tool can dispense a spot of fluid to a substrate surface by spraying the fluid from the pin. Alternatively, the transducer can cause a drop of fluid to extend from the capillary so that fluid can be passed to the substrate by contacting the drop to the surface of the substrate. Further, the tool can form an array of sample material by dispensing sample material in a series of steps, while moving the pin to different locations above the substrate surface to form the sample array. In a further embodiment, the invention then passes the prepared sample arrays to a plate assembly that disposes the sample arrays for analysis by mass spectrometry. To this end, a mass spectrometer is provided that generates a set of spectra signal which can be understood as indicative of the composition of the sample material under analysis.

In one aspect, the invention can be understood as methods for preparing an array of sample material on a surface of a substrate. The methods according to the invention can include the steps of providing a vesicle having an interior chamber containing a fluid, disposing the vesicle adjacent a first location on the surface of the substrate, controlling the vessel for delivering a nanoliter volume of a fluid at the first location of the surface of the substrate, and moving the vesicle to a set of positions adjacent to the surface substrate whereby fluid is dispensed at each location of the set of positions for forming an array of sample material.

Substrates employed during the processes of the invention can include flat surfaces for receiving the sample material as well as having surfaces that include wells formed on the surface for defining locations for receiving the fluid that can be ejected from the chambers of the vesicles. The substrates can be silicon, metal, plastic, a membrane, polymeric material, a metal-grafted polymer, as well as a substrate that is functionalized chemically, functionalized with beads, functionalized with dendrite trees of captured material, or any combinations of the above or any similar suitable material for receiving the dispensed fluid.

It is understood that the methods according to the invention can dispense both an analyte material as well as a support material, such as a matrix material, that aids in the analysis of the analyte. To this end the methods according to the invention can include the steps of depositing a matrix material onto the substance of the substrate. Further the methods can also include a step of waiting a predetermined period of time to allow a solvent of the matrix material to evaporate. Once the solvent of the matrix material has evaporated, the methods of the invention can include a step of ejecting a volume of analyte fluid into the evaporated matrix material to dissolve with the matrix material and to form a crystalline structure on the substrate surface. It is understood that this step of redissolving the matrix material with the analyte material aids in the analysis of the composition of the material during certain analytical processes, such as mass spectrometry.

In an alternate practice, the methods of the invention can include a step of dispensing a mixture that consists of the analyte material and the matrix material, as well as other material compositions. In this way the matrix and the analyte are delivered to the surface of the substrate as one volume of material. In a further step, the prepared arrays of sample material can be provided to a diagnostic tool for determining information that is representative of the composition of the sample material.

Once such diagnostic tool can include a mass spectrometer. The mass spectrometer can be a time of flight mass spectrometers, fourier transform mass spectrometers or any other suitable type of mass spectrometer that allows the analysis of composition of the sample array.

In one practice of the invention, the step of providing a vesicle having an interior chamber includes the step of providing a vesicle having a piezo electric element for causing fluid to move through the chamber. This method can also include the step of moving the vesicle by rasterizing the vesicle across the surface of the substrate, to form the array of sample material.

In an alternative practice of the invention, parallel processing protocols can be employed wherein the vesicle that is employed during the processing includes a vesicle assembly that has a plurality of vesicles arranged into a matrix for dispensing fluid to a first plurality of location on the substrate surface. In this way in a single operation, the method provides for forming a matrix a sample material on the substrate surface. In a further practice of the invention, offset printing can be employed to form a large matrix of sample material by employing multiple printing steps with the vesicle matrix. Other printing techniques can be employed by the present invention without departing from the scope thereof.

In a further practice of the invention, fluid can be dispensed to the surface of the substrate by contacting the vesicle against the surface of the substrate to spot the surface of the substrate with sample material. Alternatively, the invention provides for another non-contact printing approach wherein the processes of the invention cause a drop of fluid to be formed on at the distal tip of the vesicle. It is the drop of fluid that is contacted against the surface of the substrate for delivering sampling material thereto. This provides for the controlled delivery for the known volume of fluid without resulting in the contacting of the vesicle against the surface of the substrate.

In a further practice of the invention, vesicles are provided having an interior chamber that is dimensionally adapted to allow filling of the chamber by capillary action.

In another aspect, the invention can be understand as a method for analyzing a material, that comprises the steps of providing a vesicle suitable for carrying a fluid having the material therein, disposing the vesicle adjacent a first location of the surface of the substrate, controlling the vesicle to deliver a nanoliter volume of the fluid to provide a defined and controlled volume of fluid at the first location of the surface of the substrate, moving the vesicle to a second position adjacent a second location on the surface on the substrate to dispense a defined and controlled volume of the material along an array of locations along the substrate surface, and performing mass spectrometry analysis of the material at each location of the array. This method can include the step of mixing a matrix material and an analyte material to form the fluid being delivered to the substrate surface. Alternatively, this practice of the invention can include the steps of filling a chamber contained within the vesicle with a matrix material and dispensing the matrix material to the array of locations. Subsequently, analyte can be dispensed.

The step of performing mass spectrometry can include the step of performing a matrix assisted laser desorption ionization mass spectrometry, as well as a time of flight mass spectrometry, or a fourier transform spectrometry. In another aspect the invention can be understood as apparatus for forming an array of a sample material on a surface of a substrate. Such apparatus will comprise a vesicle having a distal end suitable for carrying a fluid thereon, a movable arm having a distal portion mounted to the vesicle, a controller for moving the arm to dispose the vesicle adjacent a first location on the surface on the substrate and for controlling the vesicle to provide a nanoliter volume of the fluid at the first location of the surface of the substrate, and a diagnostic tool for analyzing the material to generate a composition signal that is representative of the chemical composition of the material. In this apparatus the vesicle can comprise a solid shaft of material as well as a vesicle having an interior chamber suitable for carrying fluid as well as a chamber for carrying a fluid in a transducer element for ejecting fluid from that chamber. In another aspect, the invention can be understood as substrate having a surface for carrying an array of a matrix material and formed according to a process comprising the steps of a providing a vesicle suitable for transferring a fluid containing a matrix material, disposing the vesicle adjacent a first location on the surface on the substrate, controlling the vesicle of the volume fluid to the first location of the surface of the substrate, and moving a vesicle to a set of positions adjacent the surface of the substrate and delivering fluid at each of these locations to form an array of matrix material. This substrate itself can be a flat silicon chip as well as a any other suitable material, and can be pitted, include wells, and have wells that have rough interior surfaces.

BRIEF DESCRIPTION OF THE DRAWINGS

FIG. 9 depicts molecular weights determined for the sample material having spectra identified in FIG. 8.

DETAILED DESCRIPTION OF THE ILLUSTRATED EMBODIMENTS

Figure 1:
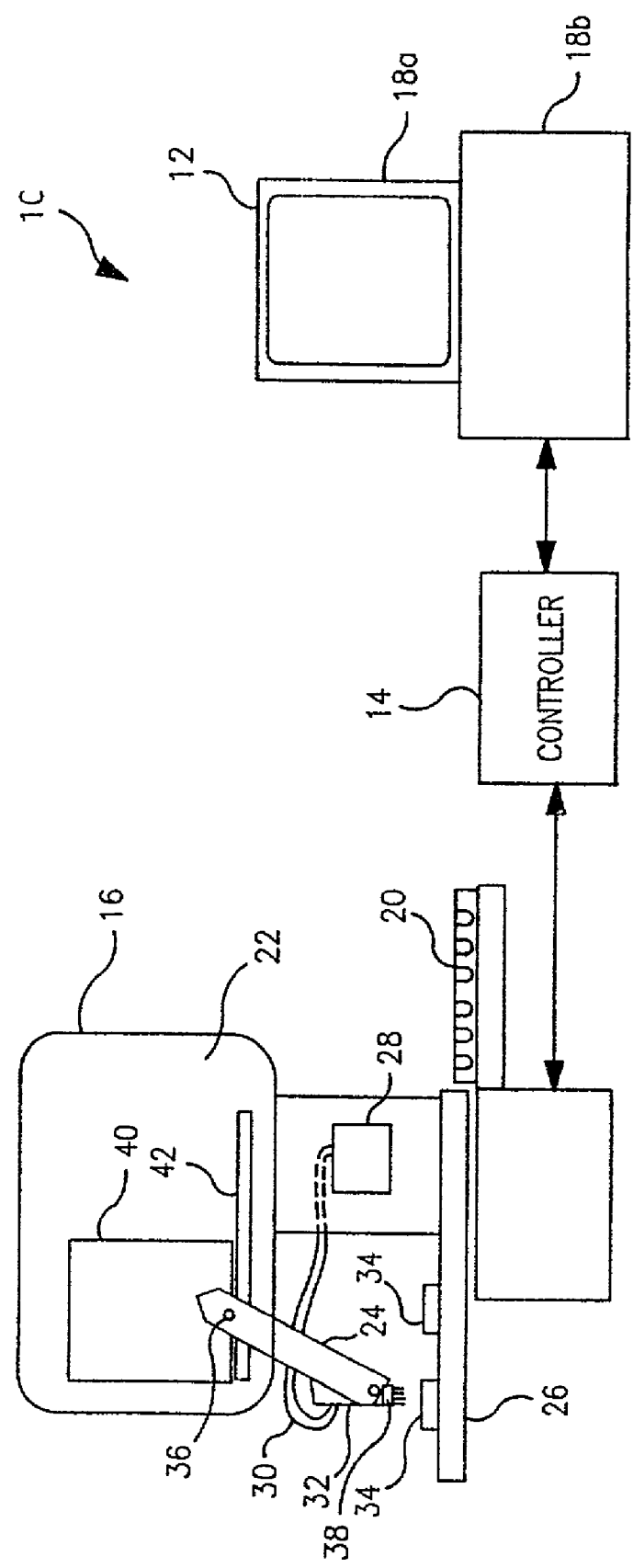
FIG. 1 illustrates one system according to the invention for preparing arrays of a sample material for analysis.

FIG. 1 illustrates one system according to the invention for preparing arrays of sample material for analysis by a diagnostic tool. FIG. 1 depicts a system 10 that includes a data processor 12, a motion controller 14, a robotic arm assembly 16, a monitor element 18A, a central processing unit 18B, a microliter plate of source material 20, a stage housing 22, a robotic arm 24, a stage 26, a pressure controller 28, a conduit 30, a mounting assembly 32, a pin assembly 38, and substrate elements 34. In the view shown by FIG. 1, it is also illustrated that the robotic assembly 16 can include a moveable mount element 40 and a horizontal slide groove 42. The robotic arm 24 can optionally pivot about a pin 36 to increase the travel range of the arm 24 so that arm 24 can disposes the pin assembly 38 above the source plate 20.

The data processor 12 depicted in FIG. 1 can be a conventional digital data processing system such as an IBM PC compatible computer system that is suitable for processing data and for executing program instructions that will provide information for controlling the movement and operation of the robotic assembly 16. It will be apparent to one skilled in the art that the data processor unit 12 can be any type of system suitable for processing a program of instructions signals that will operate the robotic assembly 16. Optionally the data processor 12 can be a microcontrolled assembly that is integrated into the robotic housing 16. In further alternative embodiments, the system 10 need not be programmable and can be a singleboard computer having a firmware memory for storing instructions for operating the robotic assembly 16.

In the embodiment depicted in FIG. 1, there is a controller 14 that electronically couples between the data processor 12 and the robotic assembly 16. The depicted controller 14 is a motion controller that drives the motor elements of the robotic assembly 16 for positioning the robotic arm 24 at a selected location. Additionally, the controller 14 can provide instructions to the robotic assembly 16 to direct the pressure controller 28 to control the volume of fluid ejected from the individual pin elements of the depicted pin assembly 38. The design and construction of the depicted motion controller 14 follows from principles well known in the art of electrical engineering, and any controller element suitable for driving the robotic assembly 16 can be practiced with the invention without departing from the scope thereof.

The robotic assembly 16 depicted in FIG. 1 electronically couples to the controller 14. The depicted robotic assembly 16 is a gantry system that includes an XY table for moving the robotic arm about an XY plane, and further includes a Z axis actuator for moving the robotic arm orthogonally to that XY plane. The robotic assembly 16 depicted in FIG. 1 includes an arm 24 that mounts to the XY stage which moves the arm within a plane defined by the XY access. In the depicted embodiment, the XY table is mounted to the Z actuator to move the entire table along the Z Axis orthogonal to the XY plane. In this way, the robotic assembly provides three degrees of freedom that allows the pin assembly 38 to be disposed to any location above the substrates 34 and the source plate 20 which are shown in FIG. 1 as sitting on the stage 26 mounted to the robotic assembly 16.

The depicted robotic assembly 16 follows from principles well known in the art of electrical engineering and is just one example of a robotic assembly suitable for moving a pin assembly to locations adjacent a substrate and source plate such as the depicted substrate 34. Accordingly, it will be apparent to one of ordinary skill in the art that alternative robotic systems can be practiced with the invention without departing from the scope thereof FIG. 1 depicts an embodiment of a robotic assembly 16 that includes a pressure controller 28 that connects via a conduit 30 to the mount 32 that connects to the pin assembly 38. In this embodiment the mount 32 has an interior channel for fluidically coupling the conduit 30 to the pin assembly 38. Accordingly, the pressure controller 28 is fluidically coupled by the conduit 30 and the mount 32 to the pin assembly 38. In this way, the controller 14 can send signals to the pressure controller 28 to control selectively a fluid pressure delivered to the pin assembly 38.

Figure 2:
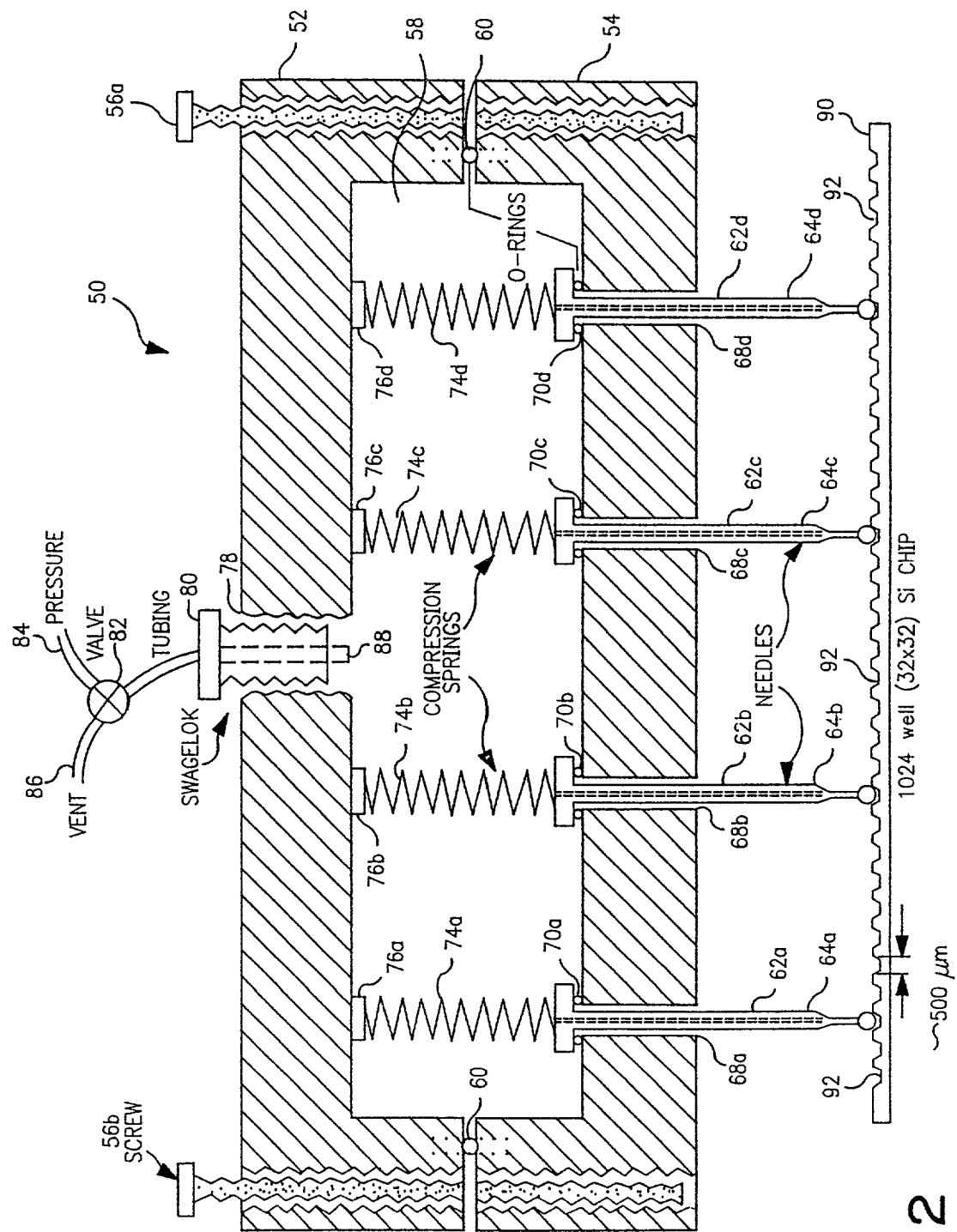
FIG. 2 illustrates a pin assembly suitable for use with the system depicted in FIG. 1 for implementing a parallel process of dispensing material to a surface of a substrate.

FIG. 2 depicts one embodiment of a pin assembly 50 suitable for practice with the system depicted in FIG. 1 which includes the pressure controller 28. In the depicted embodiment, the pin assembly 50 includes a housing formed from an upper portion 52 and a lower portion 54 that are joined together by the screws 56A and 56B to define an interior chamber volume 58. FIG. 2 further depicts that to fluidically seal the interior chamber volume 58 the housing can include a seal element depicted in FIG. 2 as an O-ring gasket 60 that sits between the upper block 52 and the lower block 54 and surrounds completely the perimeter of the interior chamber volume 58. FIG. 2 further depicts that the pin assembly 50 includes a plurality of vesicles 62A-62D, each of which include an axial bore extending therethrough to form the depicted holding chambers 64A-64D. Each of the depicted vesicles extends through a respective aperture 68A-68D disposed within the lower block 54 of the housing.

As further shown in the depicted embodiment, each of the vesicles 62A-62D has an upper flange portion that sits against a seal element 70A-70D to form a fluid-tight seal between the vesicle and the lower block 54 to prevent fluid from passing through the apertures 68A-68D. To keep the seal tight, the depicted pin assembly 50 further includes a set of biasing elements 74A-74D depicted in FIG. 2 as springs which, in the depicted embodiment, are in a compressed state to force the flange element of the vesicles 62A-62D against their respective seal elements 70A-70D. As shown in FIG. 2, the biasing elements 74A-74D extend between the vesicles and the upper block 52. Each of the springs 74A-74D can be fixedly mounted to a mounting pad 76A-76D where the spring elements can attach to the upper block 52. The upper block 52 further includes an aperture 78 depicted in FIG. 2 as a centrally disposed aperture that includes a threaded bore for receiving a swagelok 80 that can be rotatably mounted within the aperture 78.

As further depicted in FIG. 2, the swagelok 80 attaches by a conduit to a valve 82 that can connect the swagelok 80 to a conduit 84 that can be coupled to a pressure source, or alternatively can couple the swagelok 80 to a conduit 86 that provides for venting of the interior chamber 58. A central bore 88 extends through the swagelok 80 and couples to the tubing element which further connects to the valve 82 to thereby fluidically and selectively couple the interior chamber volume 58 to either a pressure source, or a venting outlet.

The pin assembly 50 described above and depicted in FIG. 2 is disposed above a substrate element 90 that includes a plurality of wells 92 that are etched into the upper surface of the substrate 90. As illustrated by FIG. 2, the pitch of the vesicles 62A-62D is such that each vesicle is spaced from the adjacent vesicles by a distance that is an integral multiple of the pitch distance between wells 92 etched into the upper surface of the substrate 90. As will be seen from the following description, this spacing facilitates the parallel dispensing of fluid, such that fluid can be dispensed into a plurality of wells in a single operation. Each of the vesicles can be made from stainless steel, silica, polymeric material or any other material suitable for holding fluid sample. In one example, 16 vesicles are employed in the assembly, which are made of hardened beryllium copper, gold plated over nickel plate. They are 43.2 mm long and the shaft of the vesicle is graduated to 0.46 mm outer diameter with a concave tip. Such a pin was chosen since the pointing accuracy (distance between the center of adjacent tips) can be approximately 501 micrometers. However, it will be apparent that any suitable pin style can be employed for the device, including but not limited to flat, star-shaped, concave, pointed solid, pointed semi-hollow, angled on one or both sides, or other such geometries.

Figure 3:
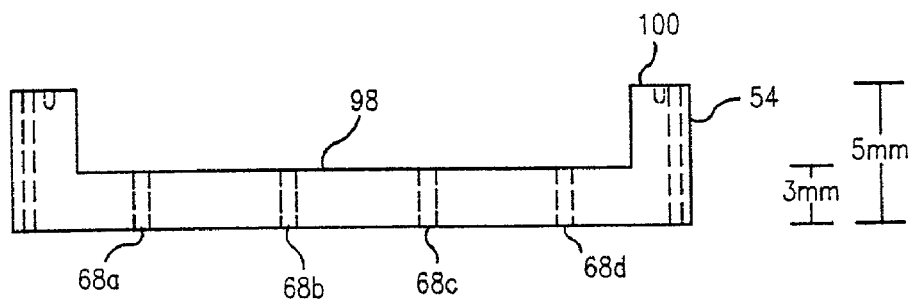
FIG. 3 depicts a bottom portion of the assembly shown in FIG. 2.

FIG. 3 shows from a side perspective the lower block 54 of the pin assembly 50 depicted in FIG. 2. FIG. 3 shows approximate dimensions for one pin assembly suited for practice with the invention. As shown, the lower block 54 has a bottom plate 98 and a surrounding shoulder 100. The bottom plate 98 is approximately 3 mm in thickness and the shoulder 100 is approximately 5 mm in thickness.

Figure 4:
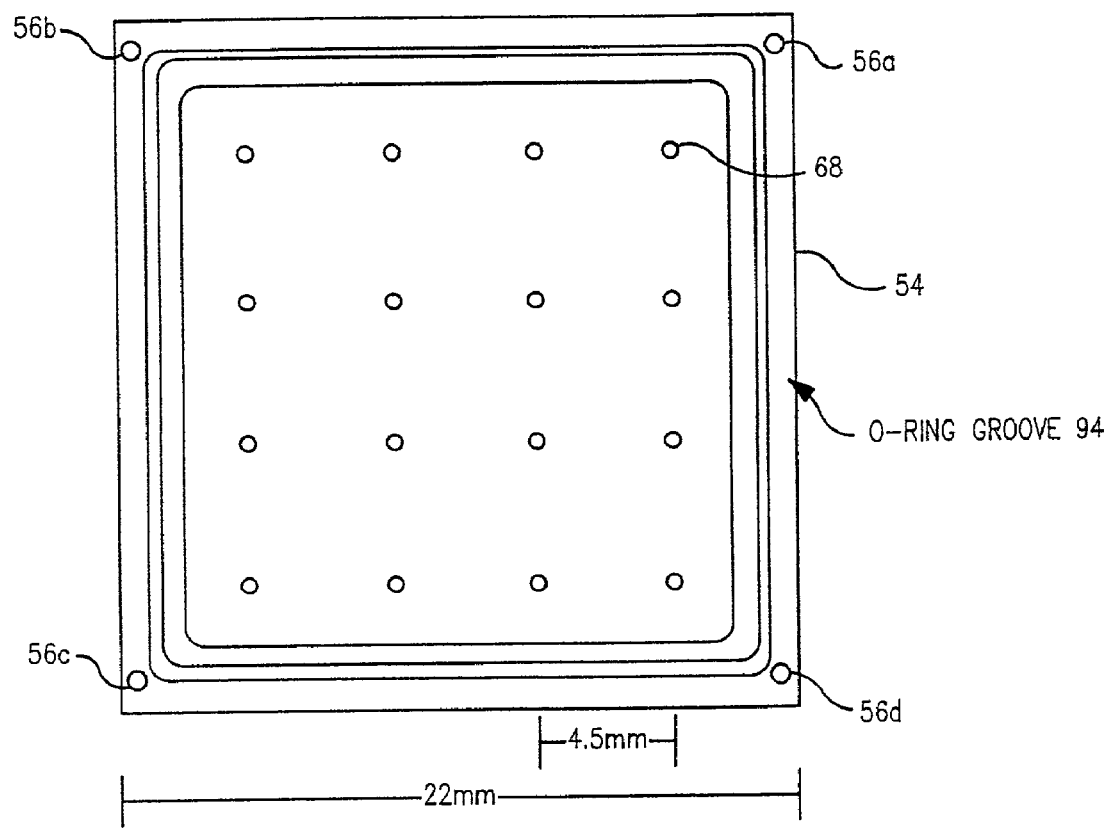
FIG. 4 depicts an alternative view of the bottom portion of the pin assembly depicted in FIG. 2.

FIG. 4 shows from an overhead perspective the general structure and dimensions for one lower block 54 suitable for use with the pin assembly 50 shown in FIG. 2. As shown in FIG. 4, the lower block 54 includes a four-by-four matrix of apertures 68 to provide 16 apertures each suitable for receiving a vesicle. As described above with reference to FIG. 2, the spacing between the aperture 68 is typically an integral multiple of the distance between wells on a substrate surface as well as the wells of a source plate. Accordingly, a pin assembly having the lower block 54 as depicted in FIG. 4 can dispense fluid in up to 16 wells simultaneously. FIG. 4 also shows general dimensions of one lower block 54 such that each side of block 54 is generally 22 mm in length and the pitch between aperture 68 is approximately 4.5 mm. Such a pitch is suitable for use with a substrate where fluid is to be dispensed at locations approximately 500 µm apart, as exemplified by the substrate 90 of FIG. 2. FIG. 4 also shows that the lower block 54 can include an optional O-ring groove 94 adapted for receiving an O-ring seal element, such as the seal element 60 depicted in FIG. 2. It is understood that such a groove element 94 can enhance and improve the fluid seal formed by the seal element 60.

The pinblock can be manufactured of stainless steel as this material can be drilled accurately to about +25 µm, but a variety of probe materials can also be used, such as G10 laminate, PMMA or other suitable material. The pin block can contain any number of apertures and is shown with 16 receptacles which hold the 16 pins in place. To increase the pointing accuracy of each pin, an optional alignment plate can be placed below the block so that about 6 mm of the pin tip is left exposed to enable dipping into the wells of a microtiter plate. The layout of the probes in the depicted tool is designed to coordinate with a 384-well microtiter plate, thus the center-to-center spacing of the probes in 4.5 mm. An array of 4×4 probes was chosen since it would produce an array that would fit in less than one square inch, which is the travel range of an xy stage of a MALDI TOF MS employed by the assignee. The pintool assembly is completed with a stainless steel cover on the top side of the device which is then attached onto the Z-arm of the robot.

With references to FIG. 5, the operation of one embodiment of the invention can be explained. In this exemplary embodiment, the robotic assembly 16 employs a pin tool assembly 38 that is configured similarly as the pin tool assembly 50 depicted in FIG. 2. The pressure controller 28 selectively controls the pressure within chamber 58. With this embodiment, a control program operates on the data processor 12 to control the robotic assembly 16 in such a way that the assembly 16 prints an array of elements on the substrates 34.

Figure 5A:
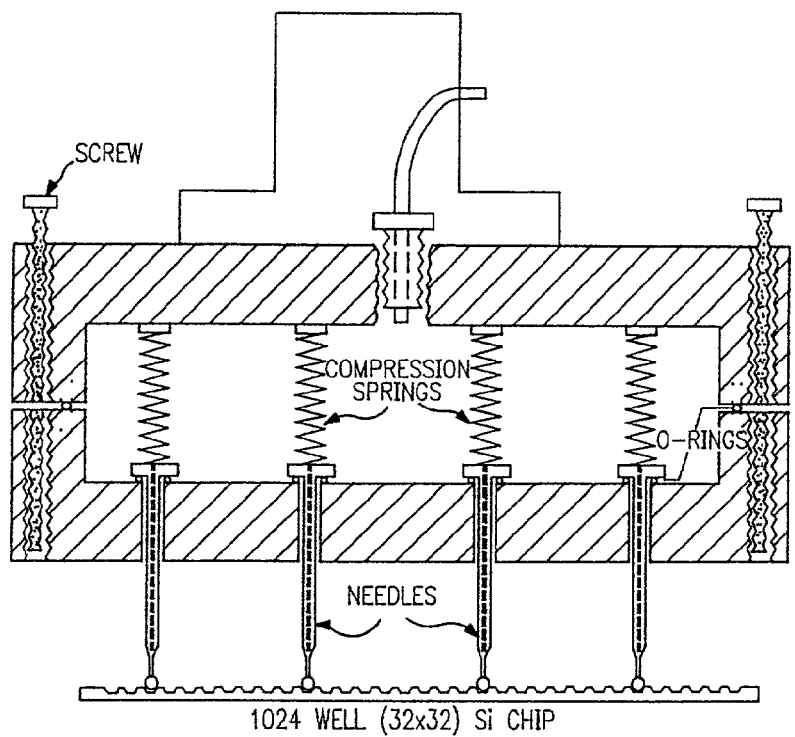
FIGS. 5A-5D depict one method according to the invention for preparing an array of sample material.

In a first step, FIG. 5A, the program can direct the robotic assembly 16 to move the pin assembly 38 to be disposed above the source plate 20. The robotic assembly 16 will then dip the pin assembly into the source plate 20 which can be a 384 well DNA source plate. As shown in FIG. 4 the pin assembly can include 16 different pins such that the pin assembly 50 will dip 16 pins into different 16 wells of the 384 well DNA source plate 20. Next, the data processor 12 will direct the motion controller 14 to operate the robotic assembly 16 to move the pin assembly to a position above the surface of the substrate 34. The substrate 34 can be any substrate suitable for receiving a sample of material and can be formed of silicon, plastic, metal, or any other such suitable material. Optionally the substrate will have a flat surface, but can alternatively include a pitted surface, a surface etched with wells or any other suitable surface typography. The program operating on data processor 12 can then direct the robotic assembly, through the motion controller 14, to direct the pressure controller 28 to generate a positive pressure within the interior chamber volume 58. In this practice, the positive interior pressure will force fluid from the holding chambers of vesicles 62 to eject fluid from the vesicles and into a respective well 92 of the substrate 90.

In this practice of the invention, the program operating on data processor 12 can also direct the controller 14 to control the pressure controller 28 to control filling the holding chambers with source material from the source plate 20. The pressure controller 28 can generate a negative pressure with respect to the ambient pressure, within the interior chamber volume 58 of the pin assembly. This will cause fluid to be drawn up into the holding chambers of the vesicles 62A-62D. The pressure controller 28 can regulate the pressure either by open-loop or closed-loop control to avoid having fluid overdrawn through the holding chambers and spilled into the interior chamber volume 58. Loop control systems for controlling pressure are well known in the art and any suitable controller can be employed. Such spillage could cause cross-contamination, particularly if the source material drawn from the source plate 20 varies from well to well.

In an alternate practice of the invention, each of the holding chambers 64A-64D is sufficiently small to allow the chambers to be filled by capillary action. In such a practice, the pin assembly can consist of an array of narrow bore needles, such as stainless steel needles, that extend through the apertures of the lower block 54. The needles that are dipped into source solutions will be filled by capillary action. In one practice, the length of capillary which is to be filled at atmospheric pressure is determined approximately by:

$$H = \frac{2\gamma}{PGR}$$

where H equals height, gamma equals surface tension, P equals solution density, G equals gravitational force and R equals needle radius. Thus the volume of fluid held by each vesicle can be controlled by selecting the dimensions of the interior bore. It is understood that at room temperature water will fill a 15 cm length of 100 µm radius capillary. Thus, a short bore nanoliter volume needle will fill to full capacity, but should not overflow because the capillary force is understood to be too small to form a meniscus at the top of the needle orifice. This prevents cross-contamination due to spillage. In one embodiment, the vesicles of the pin assembly can be provided with different sized interior chambers for holding and dispensing different volumes of fluid.

In an alternate practice, to decrease the volume of liquid that is drawn into the holding chambers of the vesicles, a small positive pressure can be provided within the interior chamber volume 58 by the pressure controller 28. The downward force created by the positive pressure can be used to counter the upward capillary force. In this way, the volume of fluid that is drawn by capillary force into the holding chambers of the vesicles can be controlled.

Figure 5B:
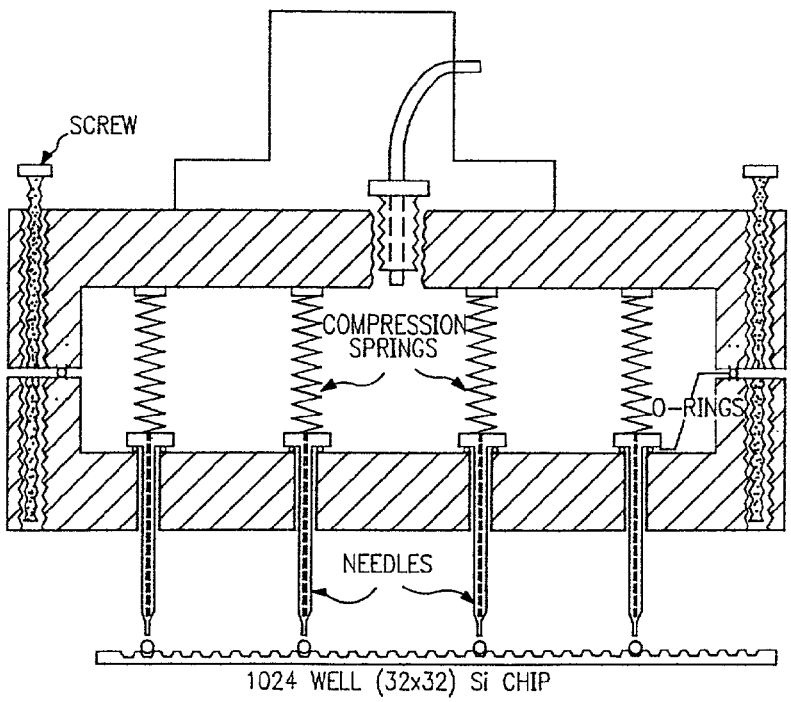

FIG. 5B, shows that fluid within the holding chambers of the needle can be dispensed by a small positive pressure introduced through the central bore 88 extending through the swagelok 80. By regulating the pressure pulse that is introduced into the interior chamber volume 58, fluid can be ejected either as a spray or by droplet formation at the needle tip. It is understood that the rate of dispensing, droplet versus spray, depends in part upon the pressure applied by the pressure controller 28. In one practice, pressure is applied in the range of between 10 and 1,000 Torr of atmospheric pressure.

To this end the data processor 12 can run a computer program that controls and regulates the volume of fluid dispensed. The program can direct the controller 28 to eject a defined volume of fluid, either by generating a spray or by forming a drop that sits at the end of the vesicle, and can be contacted with the substrate surface for dispensing the fluid thereto.

Figure 5C:
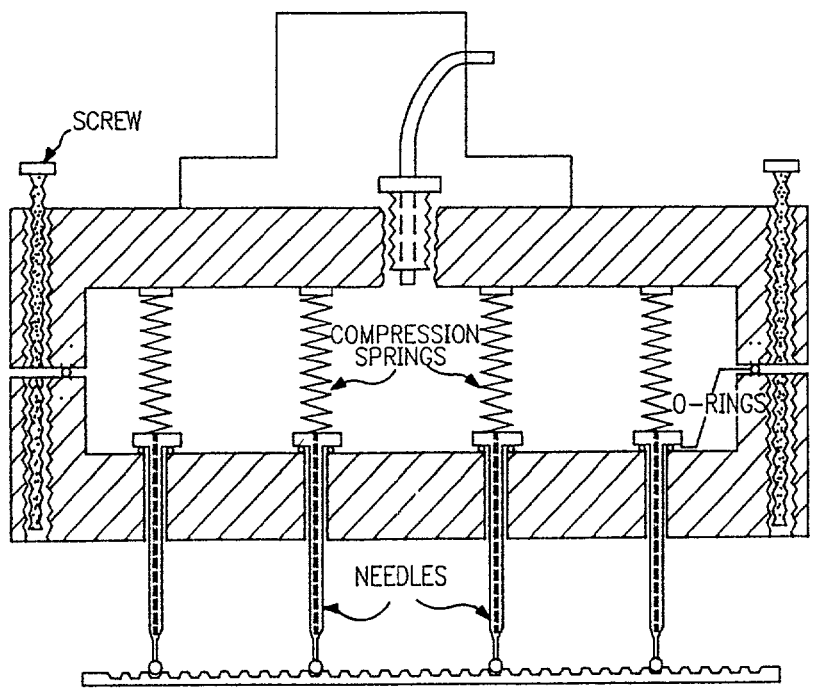
Figure 5D:
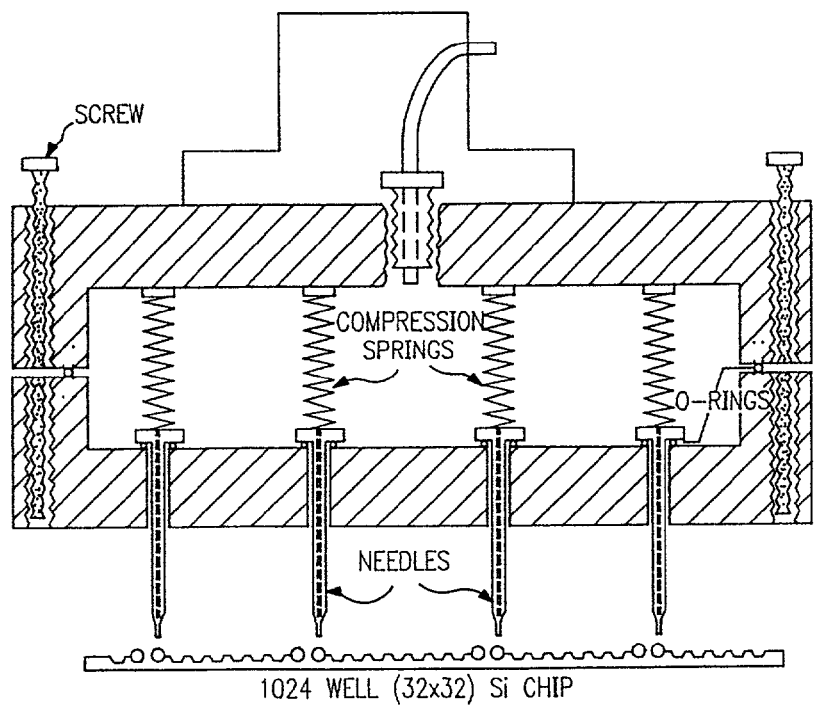

FIGS. 5C and 5D show the earlier steps shown in FIGS. 5A-5B can again be performed, this time at a position on the substrate surface that is offset from the earlier position. In the depicted process, the pin tool is offset by a distance equal to the distance between two wells 92. However, it will be apparent that other offset printing techniques can be employed without departing from the scope of the invention.

It will be understood that several advantages of the pin assembly depicted in FIG. 2 are achieved. For example, rinsing between dispensing events is straightforward, requiring only single or multiple pin fillings and emptying events with a rinse solution. Moreover, since all holding chambers fill to full capacity, the accuracy of the volumes dispensed varies only according to needle inner dimensions which can be carefully controlled during pin production. Further, the device is cost effective, with the greatest expense attributed to the needles, however because no contact with a surface is required, the needles are exposed to little physical strain or stress, making replacement rare and providing long life.

Alternatively, deposition of sample material onto substrate surface can include techniques that employ pin tool assemblies that have solid pin elements extending from a block wherein a robotic assembly dips the solid pin elements of the pin assembly into a source of sample material to wet the distal ends of the pins with the sample materials. Subsequently the robotic assembly can move the pin assembly to a location above the surface the substrate and then lower the pin assembly against the surface of the substrate to contact the individual wetted pins against the surface for spotting material of the substrate surface.

Figure 6A:
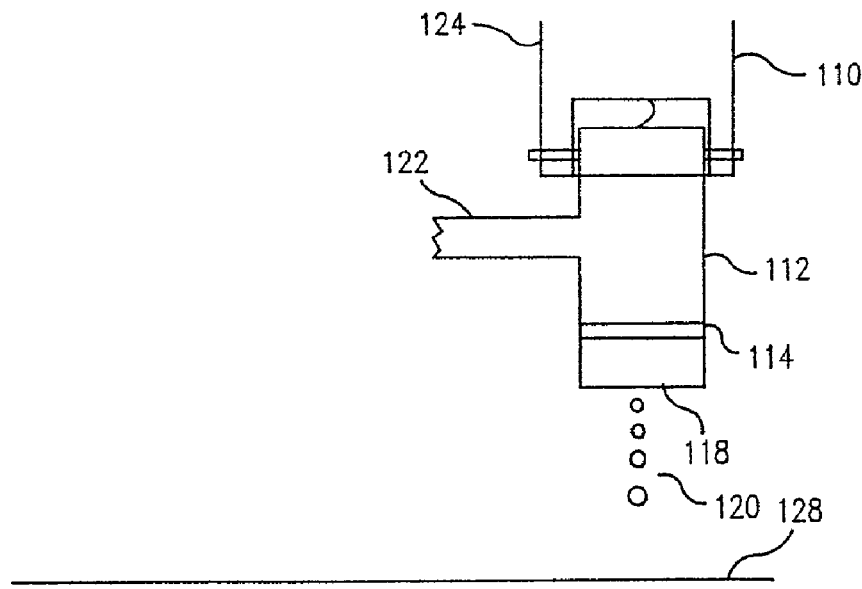
FIGS. 6A-6B depict an alternative assembly for dispensing material to the surface of a substrate.
Figure 6B:
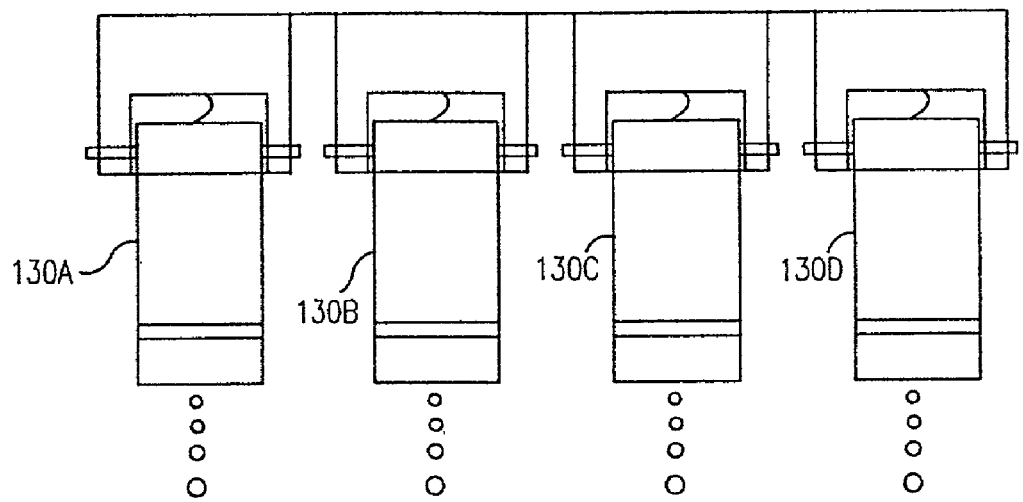

FIGS. 6A and 6B depict another alternative system for dispensing material on or to the surface of the substrate. In particular, FIG. 6A depicts a jet printing device 110 which includes a capillary element 112, a transducer element 114 and orifice (not shown) 118, a fluid conduit 122, and a mount 124 connecting to a robotic arm assembly, such as the robotic arm 24 depicted in FIG. 1. As further shown in FIG. 6A the jet assembly 110 is suitable for ejecting from the orifice 118a series of drops 120 of a sample material for dispensing sample material onto the surface 128.

The capillary 112 of the jet assembly 110 can be a glass capillary, a plastic capillary, or any other suitable housing that can carry a fluid sample and that will allow the fluid sample to be ejected by the action of a transducer element, such as the transducer element 114. The transducer element 114 depicted in FIG. 6A is a piezo electric transducer element which forms around the parameter of the capillary 112 and can transform an electrical pulse received from the pulse generator within a robotic assembly 16 to cause fluid to eject from the orifice 118 of the capillary 112. One such jet assembly having a piezoelectric transducer element is manufactured by MicroFab Technology, Inc., of Germany. However any jet assembly that is suitable for dispensing defined and controlled the volumes of fluid can be practiced with the invention including those that use piezoelectric transducers, electric transducers, electrorestrictive transducers, magnetorestrictive transducers, electromechanical transducers, or any other suitable transducer element. In the depicted embodiment, the capillary 112 has a fluid conduit 122 for receiving fluid material. In an optional embodiment, fluid can be drawn into the capillary by action of a vacuum pressure that will draw fluid through the orifice 118 when the orifice 118 is submerged in a source of fluid material. Other embodiments of the jet assembly 110 can be practiced with the invention without departing from the scope thereof.

FIG. 6B illustrates a further alternative assembly suitable for practice with the invention, and suitable for being carried on the robotic arm of a robotic assembly, such as the assembly 16 depicted in FIG. 1. FIG. 6B illustrates four jet assemblies connected together, 130A-130D. Similar to the pin assembly in FIG. 2, the jet assembly depicted in FIG. 6B can be employed for the parallel dispensing of fluid material. It will be obvious to one of ordinary skill in the art of electrical engineering, that each of the jet assemblies 130A-130D can be operated independently of the others, for allowing the selective dispensing of fluid from select ones of the jet assemblies. Moreover, each of the jet assemblies 130A-130D can be independently controlled to select the volume of fluid that is dispensed from each respected one of the assembly 130A-130D Other modifications and alternations can be made to the assembly depicted in FIG. 6B without departing from the scope of the invention.

In another aspect, the invention provides methods for rapidly analyzing sample materials. To this end sample arrays can be formed on a substrate surface according to any of the techniques discussed above. The sample arrays are then analyzed by mass spectrometry to collect spectra data that is representative of the composition of the samples in the array. It is understood that the above methods provide processes that allow for rapidly dispensing definite and controlled volumes of analyte material. In particular these processes allow for dispensing sub to low nanoliter volumes of fluid. These low volume deposition techniques generate sample arrays well suited for analysis by mass spectrometry. For example, the low volumes yield reproducibility of spot characteristics, such as evaporation rates and reduced dependence on atmospheric conditions such as ambient temperature and light.

Continuing with the example shown in FIG. 1, the arrays can be prepared by loading oligonucleotides (0.1-50 ng/lll) of different sequences or concentrations into the wells of a 96 well microtiter source plate 20; the first well can be reserved for holding a matrix solution. A substrate 34, such as a pitted silicon chip substrate, can be placed on the stage 26 of the robotics assembly 16 and can be aligned manually to orient the matrix of wells about a set of reference axes. The control program executing on the data processor 12 can receive the coordinates of the first well of the source plate 20. The robotic arm 12 can dip the pin assembly 38 into source plate 20 such that each of the 16 pins is dipped into one of the wells. Each vesicle can fill by capillary action so that the full volume of the holding chamber contains fluid. Optionally, the program executing on the data processor 12 can direct the pressure controller to fill the interior chamber 58 of the pin assembly 38 with a positive bias pressure that will counteract, in part, the force of the capillary action to limit or reduce the volume of fluid that is drawn into the holding chamber.

Optionally, the pin assembly 38 can be dipped into the same 16 wells of the source plate 20 and spotted on a second target substrate. This cycle can be repeated on as many target substrates as desired. Next the robotic arm 24 can dip the pin assembly 38 in a washing solution, and then dip the pin assembly into 16 different wells of the source plate 20, and spot onto the substrate target offset a distance from the initial set of 16 spots. Again this can be repeated for as many target substrates as desired. The entire cycle can be repeated to make a 2×2 array from each vesicle to produce an 8×8 array of spots (2×2 elements/vesicle×16 vesicles=64 total elements spotted). However, it will be apparent to anyone of ordinary skill in the art that process suitable for forming arrays can be practiced with the present invention without departing from the scope thereof.

In an alternative practice of the invention, oligonucleotides of different sequences or concentrations can be loaded into the wells of up to three different 384-well microtiter source plates; one set of 16 wells can be reserved for matrix solution. The wells of two plates are filled with washing solution. Five microtiter plates can be loaded onto the stage of the robotic assembly 16. A plurality of target substrates can be placed abutting an optional set of banking or registration pins disposed on the stage 26 and provided for aligning the target substrates along a set of reference axes. If the matrix and oligonucleotide are not pre-mixed, the pin assembly can be employed to first spot matrix solution on all desired target substrates. In a subsequent step the oligonucleotide solution can be spotted in the same pattern as the matrix material to re-dissolve the matrix. Alternatively, a sample array can be made by placing the oligonucleotide solution on the wafer first, followed by the matrix solution, or by-pre-mixing the matrix and oligonucleotide solutions.

After depositing the sample arrays onto the surface of the substrate, the arrays can be analyzed using any of a variety of means (e.g., spectrometric techniques, such as UV/VIS, IR, fluorescence, chemiluminescence, NMR spectroscopy or mass spectrometry. For example, subsequent to either dispensing process, sample loaded substrates can be placed onto a MALDI-TOF source plate and held there with a set of beveled screw mounted polycarbonate supports. In one practice, the plate can be transferred on the end of a probe to be held onto a 1 μm resolution, 1" travel xy stage (Newport) in the source region of a time-of-flight mass spectrometer. It will be apparent to one of ordinary skill in the art that any suitable mass spectrometry tool can be employed with the present invention without departing from the scope thereof.

Preferred mass spectrometer formats for use in the instant invention include ionization (I) techniques including but not limited to matrix assisted laser desorption (MALDI), continuous or pulsed electrospray (ESI) and related methods (e.g. Ionspray or Thermospray), or massive cluster impact (MCI); those ion sources can be matched with detection formats including linear or non-linear reflectron time-of-flight (TOF), single or multiple quadruple, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected for example, using ESI (Valaskovic, G. A. et al., (1996) Science 273: 1199-1202) or MALDI (Li, L. et al., (1996) J. Am. Chem. Soc. 118: 1662-1663) mass spectrometry.

Thus, it will be understood that in processes according to the invention a completely non-contact, high-pressure spray or partial-contact, low-pressure droplet formation mode can be employed. In the latter, the only contact that will occur is between the droplet and the walls of the well or a hydrophilic flat surface of the substrate 34. However, in neither practice need there be any contact between the needle tip and the surface.

Definitions

As used herein the following terms and phrases shall have the meanings set forth below:

As used herein, the term "nucleic acid" refers to oligonucleotides or polynucleotides such as deoxyribonucleic acid (DNA) and ribonucleic acid (RNA) as well as analogs of either RNA or DNA, for example made from nucleotide analog, any of which are in single or double-stranded form. Nucleic acid molecules can be synthetic or can be isolated from a particular biological sample using any of a number or procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994)).

The terms "protein" "polypeptide" and "peptide" are used interchangeably herein when referring to a translated nucleic acid (e.g. a gene product).

"Sample" as used herein, shall refer to a composition containing a material to be detected. In a preferred embodiment, the sample is a "biological sample" (i.e., any material obtained from a living source (e.g. human, animal, plant, bacteria, fungi, protist, virus). The biological sample can be in any form, including solid materials (e.g. tissue, cell pellets and biopsies) and biological fluids (e.g. urine, blood, saliva, amniotic fluid and a mouth wash (containing buccal cells)). Preferably solid materials are mixed with a fluid.

"Substrate" shall mean an insoluble support onto which a sample is deposited according to the materials of the invention. Examples of appropriate substrates include beads (e.g., silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without filter plates.

EXAMPLES

Robot-driven serial and parallel pL-nL dispensing tools were used to generate 10-$10^3$ element DNA arrays on <1" square chips with flat or geometrically altered (e.g. with wells) surfaces for matrix assisted laser desorption ionization mass spectrometry analysis. In the former, a 'piezoelectric pipette' (70 μm id capillary) dispenses single or multiple ~0.2 nL droplets of matrix, and then analyte, onto the chip; spectra from as low as 0.2 fmol of a 36-mer DNA have been acquired using this procedure. Despite the fast (<5 sec) evaporation, micro-crystals of 3-hydroxypicolinic acid matrix containing the analyte are routinely produced resulting in higher reproducibility than routinely obtained with larger volume preparations; all of 100 five fmol spots of a 23-mer in 800 μm wells yielded easily interpreted mass spectra, with 99/100 parent ion signals having signal to noise ratio of >5. In a second approach, probes from a 384 well microtiter plate are dispensed 16 at a time into chip wells or onto flat surfaces using an array of spring loaded pins which transfer ~20 nL to the chip by surface contact; MS analysis of array elements deposited with the parallel method are comparable in terms of sensitivity and resolution to those made with the serial method.

I. Description of the piezoelectric serial dispenser. The experimental system built on a system purchased from Microdrop GmbH, Norderstedt Germany and consists of a piezoelectric element driver which sends a pulsed signal to a piezoelectric element bonded to and surrounding a glass capillary which holds the solution to be dispensed; a pressure transducer to load (by negative pressure) or empty (by positive pressure) the capillary; a robotic xyz stage and robot driver to maneuver the capillary for loading, unloading, dispensing, and cleaning; a stroboscope and driver pulsed at the frequency of the piezo element to enable viewing of 'suspended' droplet characteristics; separate stages for source and designation plates or sample targets (i.e. Si chip); a camera mounted to the robotic arm to view loading to designation plate; and a data station which controls the pressure unit, xyz robot, and piezoelectric driver.

II. Description of the parallel dispenser. The robotic pintool consists of 16 probes housed in a probe block and mounted on an X Y, Z robotic stage. The robotic stage was a gantry system which enables the placement of sample trays below the arms of the robot. The gantry unit itself is composed of X and Y arms which move 250 and 400 mm, respectively, guided by brushless linear servo motors with positional feedback provided by linear optical encoders. A lead screw driven Z axis (50 mm vertical travel) is mounted to the xy axis slide of the gantry unit and is controlled by an in-line rotary servo motor with positional feedback by a motor-mounted rotary optical encoder. The work area of the system is equipped with a slide-out tooling plate that holds five microtiter plates (most often, 2 plates of wash solution and 3 plates of sample for a maximum of 1152 different oligonucleotide solutions) and up to ten 20×20 mm wafers. The wafers are placed precisely in the plate against two banking pins and held secure by vacuum. The entire system is enclosed in plexi-glass housing for safety and mounted onto a steel support frame for thermal and vibrational damping. Motion control is accomplished by employing a commercial motion controller which was a 3-axis servo controller and is integrated to a computer; programming code for specific applications is written as needed.

Samples were dispensed with the serial system onto several surfaces which served as targets in the MALDI TOF analysis including; [1] A flat stainless steel sample target as supplied for routine use in a Thermo Bioanalysis Vision 2000; [2] the same design stainless steel target with micromachined nanopits; [3] flat silicon (Si) wafers; [4] polished flat Si wafers; [5] Si wafers with rough (3-6 pLm features) pits; [6] (a) 12×12 (or (b) 18×18) mm Si chips with (a)10×10 (or (b) 16×16) arrays of chemically etched wells, each 800×8001 ln on a side with depths ranging from 99-400 (or (b) 120) micrometer, pitch (a) 1.0 (or (b) 1.125) mm; [7] 15×15 mm Si chips with 28×28 arrays of chemically etched wells, each 450×450 micrometer on a side with depths ranging from 48-300 micrometer, pitch 0.5 mm; [8] flat polycarbonate or other plastics; [9] gold and other metals; [10] membranes; [11] plastic surfaces sputtered with gold or other conducting materials. The dispensed volume is controlled from $10^{-10}$ to $10^{-6}$ L by adjusting the number of droplets dispensed Sample Preparation and Dispensing: Serial. Oligonucleotides (0.1-50 ng/microliter) of different sequence or concentrations were loaded into wells of a 96 well microtiter plate; the first well was reserved for matrix solution. A pitted chip (target 6a in 'MALDI targets' section) was placed on the stage and aligned manually. Into the (Windows-based) robot control software were entered the coordinates of the first well, the array size (ie number of spots in x and y) and spacing between elements, and the number of 0.2 nL drops per array element. The capillary was filled with ~10 microL rinse $H_2O$, automatically moved in view of a strobe light-illuminated camera for checking tip integrity and cleanliness while in continuous pulse mode, and emptied. The capillary was then filled with matrix solution, again checked at the stroboscope, and then used to spot an array onto flat or pitted surfaces. For reproducibility studies in different MS modes, typically a 10×10 array of 0.2-20 nL droplets were dispensed. The capillary was emptied by application of positive pressure, optionally rinsed with H2O, and led to the source oligo plate where ~5 µL of 0.05-2.0 µM synthetic oligo were drawn. The capillary was then rastered in series over each of the matrix spots with 0.2-20 nL aqueous solution added to each.

Sample Preparation and Dispensing: Paraelle. Programs were written to control array making by offset printing; to make an array of 64 elements on 10 wafers, for example, the tool was dipped into 16 wells of a 384 well DNA source plate, moved to the target (e.g. Si, plastic, metal), and the sample spotted by surface contact. The tool was then dipped into the same 16 wells and spotted on the second target; this cycle was repeated on all ten wafers. Next the tool was dipped in washing solution, then dipped into 16 different wells of the source plate, and spotted onto the target 2.25 mm offset from the initial set of 16 spots; again this as repeated on all 10 wafers; the entire cycle was repeated to make a 2×2 array from each pin to produce an 8×8 array of spots (2×2 elements/pin×16 pins =64 total elements spotted).

To make arrays for MS analysis, oligonucleotides of different sequences or concentrations were loaded into the wells of up to three different 384-well microtiter plates; one set of 16 wells was reserved for matrix solution. The wells of two plates were filled with washing solution. The five microtiter plates were loaded onto the slide-out tooling plate. Ten wafers were placed abutting the banking pins on the tooling plate, and the vacuum turned on. In cases where matrix and oligonucleotide were not pre-mixed, the pintool was used to spot matrix solution first on all desired array elements of the ten wafers. For this example, a 16×16 array was created, thus the tool must spot each of the ten wafers 16 times, with an offset of 1.125 mm. Next, the oligonucleotide solution was spotted in the same pattern to re-dissolve the matrix. Similarly, an array could be made by placing the oligonucleotide solution on the wafer first, followed by the matrix solution, or by-pre-mixing the matrix and oligonucleotide solutions.

Mass Spectrometry. Subsequent to either dispensing scheme, loaded chips were held onto a MALDI-TOF source plate with a set of beveled screw mounted polycarbonate supports. The plate was transferred on the end of a probe to be held onto a 1 µm resolution, 1" travel xy stage (Newport) in the source region of a time-of-flight mass spectrometer. The instrument, normally operated with 18-26 kV extraction, could be operated in linear or curved field reflectron mode, and in continuous or delayed extraction mode.

Observations

I. Serial dispensing with the piezoelectric pipette. While delivery of a saturated 3HPA solution can result in tip clogging as the solvent at the capillary-air interface evaporates, pre-mixing DNA and matrix sufficiently dilutes the matrix such that it remains in solution while stable sprays which could be maintained until the capillary was emptied were obtained; with a 1:1 diluted (in $H_2O$) matrix solution, continuous spraying for >>10 minutes was possible. Turning off the piezo element so that the capillary sat inactive for >5 minutes, and reactivating the piezo element also did not result in a clogged capillary.

Initial experiments using stainless steel sample targets as provided by Finnigan Vision 2000 MALDI-TOF system run in reflectron mode utilized a pre-mixed solution of the matrix and DNA prior to dispensing onto the sample target. In a single microtiter well, 50 µL saturated matrix solution, 25 µL of a 51 µL solution of the 12-mer (ATCG)3, and 25 µL of a 51 µL solution of the 28-mer (ATCG)7 were mixed. A set of 10×10 arrays of 0.6 µL drops was dispensed directly onto a Finnigan Vision 2000 sample target disk; MALDI-TOF mass spectrum was obtained from a single array element which contained 750 attomoles of each of the two oligonucleotides. Interpretable mass spectra has been obtained for DNAs as large as a 53-mer (350 amol loaded, not shown) using this method.

Figure 7:
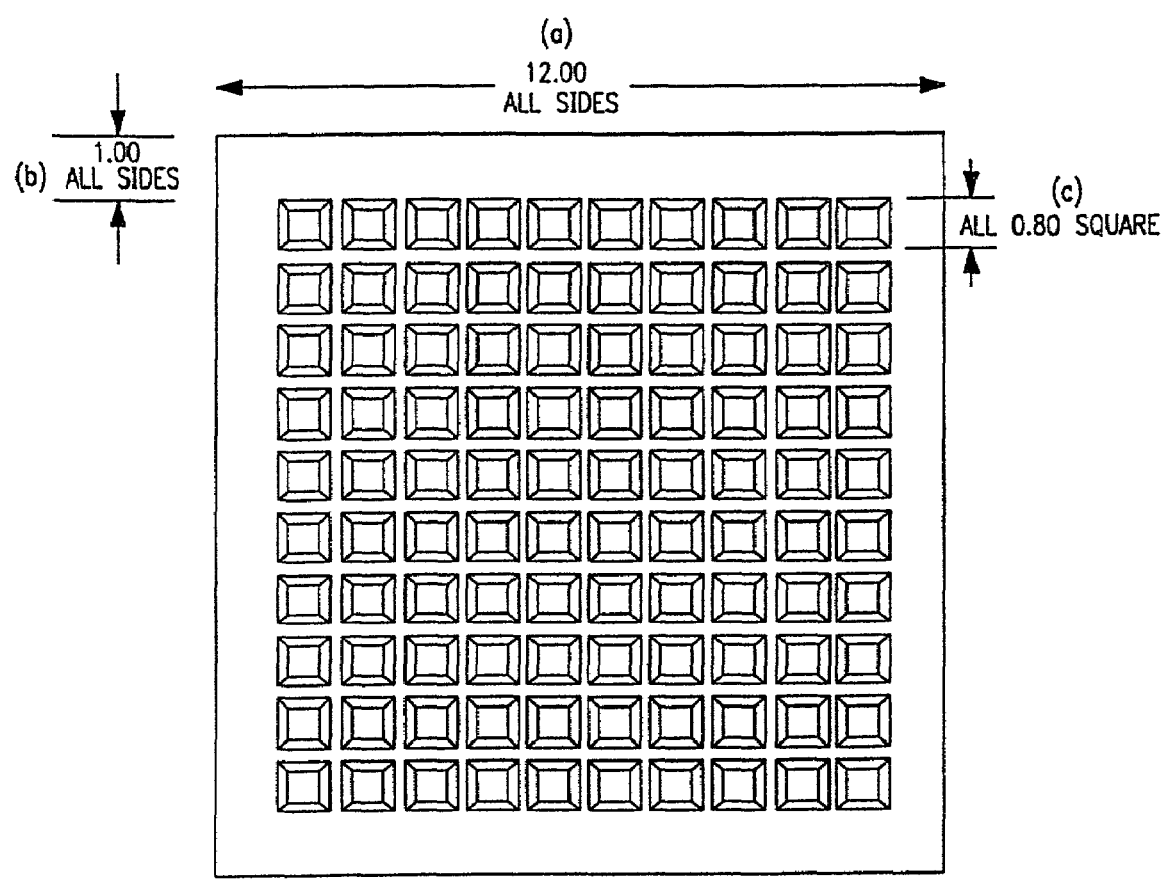
FIG. 7 depicts one embodiment of a substrate having wells etched therein that are suitable for receiving material for analysis.

Mass spectra were also obtained from DNAs microdispensed into the wells of a silicon chip. FIG. 7 shows a 12×12 mm silicon chip with 100 chemically etched wells; mask dimensions and etch time were set such that fustum (ie, inverted flat top pyramidal) geometry wells with 800×800 µm (top surface) and 100 µm depth were obtained. Optionally, the wells can be roughed or pitted. As described above, the chip edge was aligned against a raised surface on the stage to define the x and y coordinate systems with respect to the capillary. (Alternatives include optical alignment, artificial intelligence pattern recognition routines, and dowel-pin based manual alignment). Into each well was dispensed 20 droplets (~5 nL) of 3-HPA matrix solution without analyte; for the 50% $CH_3CN$ solution employed, evaporation times for each droplet were on the order of 5-10 seconds. Upon solvent evaporation, each microdispensed matrix droplet as viewed under a 120× stereomicroscope generally appeared as an amorphous and 'milky' flat disk; such appearances are consistent with those of droplets from which the FIG. 3b spectrum was obtained. Upon tip emptying, rinsing, and refilling with a 1.4 µM aqueous solution of a 23-mer DNA ($M_r$(calc)=6967 Da), the capillary was directed above each of the 100 spots of matrix where 5 nL of the aqueous DNA solution was dispensed directly on top of the matrix droplets. Employing visualization via a CCD camera, it appeared that the aqueous analyte solution mixed with and re-dissolved the matrix (complete evaporation took ~10 sec at ambient temperature and humidity). The amorphous matrix surfaces were converted to true micro-crystalline surfaces, with crystalline features on the order of <1 µm.

Figure 8:
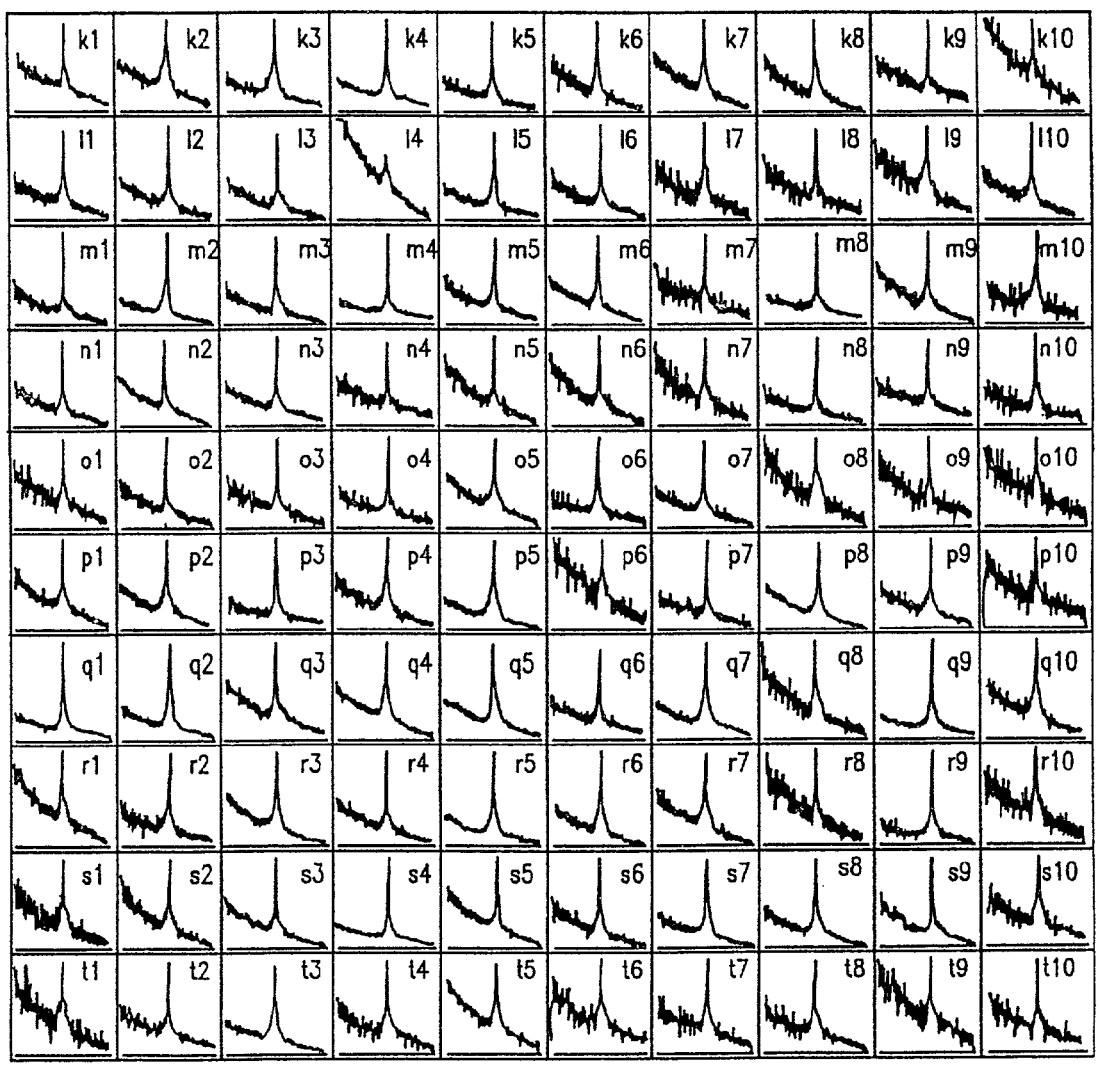
FIG. 8 depicts one example of spectra obtained from a linear time of flight mass spectrometer instrument and representative of the material composition of the sample material on the surface of the substrate depicted in FIG. 7.

Consistent with the improved crystallization afforded by the matrix re-dissolving method, mass spectrum acquisition appeared more reproducible than with pre-mixed matrix plus analyte solutions; each of the 100 five fmol spots of the 23-mer yielded interpreted mass spectra (FIG. 8), with 99/100 parent ion signals having signal to noise ratio of >5; such reproducibility was also obtained with the flat silicon and metallic surfaces tried (not shown). The FIG. 8 spectra were obtained on a linear TOF instrument operated at 26 kV. Upon internal calibration of the top left spectrum (well 'k1') using the singly and doubly charged molecular ions, and application of this calibration file to all other 99 spectra as an external calibration (FIG. 9), a standard deviation of <9 Da from the average molecular weight was obtained, corresponding to a relative standard deviation of ~0.1%.

II. Parallel Dispensing with the robotic pintool. Arrays were made with offset printing as described above. The velocity of the X and Y stages are 35 inches/sec, and the velocity of the Z stage is 5.5 inches/sec. It is possible to move the X and Y stages at maximum velocity to decrease the cycle times, however the speed of the Z stage is to be decreased prior to surface contact with the wafer to avoiding damaging it. At such axes speeds, the approximate cycle time to spot 16 elements (one tool impression of the same solutions) on all ten wafers is 20 seconds, so to make an array of 256 elements would take 5.3 minutes. When placing different oligonucleotide solutions on the array, an additional washing step must be incorporated to clean the pin tip prior to dipping in another solution, thus the cycle time would increase to 25 seconds or 6.7 minutes to make 10 wafers.

Sample delivery by the tool was examined using radiolabeled solutions and the phosphorimager as described previously; it was determined that each pin delivers approximately 1 nL of liquid. The spot-to-spot reproducibility is high. An array of 256 oligonucleotide elements of varying sequence and concentration was made on flat silicon wafers using the pintool, and the wafer was analyzed by MALDI-TOF MS.

It will be understood that the above described examples and illustrated embodiments are provided for describing the invention set forth herein and are not to be taken as limiting in any way, and the scope of the invention is to understood by the claims.

We claim:

1. A process for preparing a substrate having an array of spots having matrix for matrix-assisted laser-desorption ionization (MALDI) mass spectrometry and no analyte, which comprises:
    (a) depositing a defined and controlled 0.2 to 20 nanoliter volume of a solution comprising 3-hydroxypicolinic acid matrix, an evaporating solvent and no analyte at a plurality of discrete locations on the surface of a substrate by an automated dispenser; and
    (b) evaporating the solvent, thereby forming an array of spots on the surface of the substrate comprising the matrix and no analyte.

2. The process of claim 1, wherein the substrate comprises material selected from the group consisting of silica, glass, cellulose, silicon, metal, plastic, polymer and metal-grafted polymer.

3. The process of claim 2, wherein the substrate comprises silicon.

4. The process of claim 2, wherein the substrate comprises a metal.

5. The process of claim 2, wherein the substrate comprises a plastic.

6. The process of claim 2, wherein the substrate comprises a metal-grafted polymer.

7. The process of claim 1, wherein the substrate is selected from the consisting of a flat surface, a flat surface with pits, a solid or porous bead, a membrane or a pin.

8. The process of claim 7, wherein the substrate comprises a flat surface.

9. The process of claim 7, wherein the substrate comprises a membrane.

10. The process of claim 1, wherein the substrate is chemically functionalized.

11. The process of claim 10, wherein the substrate is chemically functionalized with beads.

12. The process of claim 10, wherein the substrate is chemically functionalized with a dendritic material.

13. The process of claim 1, wherein the substrate is a chip.

14. The process of claim 13, wherein the substrate is a silicon chip.

15. The process of claim 1, wherein each spot is a flat disk.

16. The process of claim 1, wherein the spot size is defined by square dimensions of 800 micrometers by 800 micrometers or less.

17. The process of claim 1, wherein the spot size is defined by square dimensions of 450 micrometers by 450 micrometers or less.

18. The process of claim 1, wherein each spot consists essentially of the matrix after the solvent has evaporated.

19. The process of claim 18, wherein each spot consists of the matrix after the solvent has evaporated.

20. The process of claim 1, wherein the solvent comprises water.

21. The process of claim 20, wherein the solvent is water.

22. The process of claim 1, wherein the solvent comprises $CH_3CN$.

23. The process of claim 22, wherein the solvent is 50% $CH_3CN$.

24. The process of claim 1, wherein the solution comprising the matrix is a saturated matrix solution.

25. The process of claim 1, wherein the solution comprising the matrix is a diluted matrix solution.

26. The process of claim 1, wherein the automated dispenser comprises a vesicle having a chamber and a transducer element for ejecting fluid from the chamber.

27. The process of claim 26, wherein the transducer element is selected from the group consisting of piezoelectric, electric, electrorestrictive, magnetorestrictive, electrochemical transducers and the like.

28. The process of claim 27, wherein the transducer element is a piezoelectric transducer.

29. The process of claim 1, wherein the automated dispenser deposits the solution without touching the surface of the substrate.

30. The process of claim 1, wherein the automated dispenser comprises vesicle that comprises a pin having a chamber of sufficient narrow bore to allow the chamber to at least partially fill with a solution by capillary action.

31. The process of claim 1, wherein the automated dispenser deposits the solution by contacting the surface of the substrate.

32. The process of claim 1, wherein the automated dispenser comprises a vesicle that comprises a solid shaft of material.

33. The process of claim 1, wherein the automated dispenser comprises a vesicle that is rastered over the surface of the substrate.

34. The process of claim 1, wherein the automated dispenser comprises a plurality of vesicles in an array.

* * * * *

UNITED STATES PATENT AND TRADEMARK OFFICE
CERTIFICATE OF CORRECTION

PATENT NO.        : 7,285,422 B1                                   Page 1 of 1
APPLICATION NO. : 08/786988
DATED             : October 23, 2007
INVENTOR(S)       : Daniel P. Little et al.

It is certified that error appears in the above-identified patent and that said Letters Patent is hereby corrected as shown below:

In Claim 7, please insert the word -- group -- after "selected from the" and before "consisting of a flat surface".

In Claim 30, please insert the word -- a -- after "dispenser comprises" and before "vesicle that comprises".

Signed and Sealed this

Third Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,285,422 B1 | Page 1 of 1 |
| APPLICATION NO. | : 08/786988 | |
| DATED | : October 23, 2007 | |
| INVENTOR(S) | : Daniel P. Little et al. | |

It is certified that error appears in the above-identified patent and that said Letters Patent is hereby corrected as shown below:

Column 18, Claim 7, line 18, please insert the word -- group -- after "selected from the" and before "consisting of a flat surface".

Column 19, Claim 30, line 5, please insert the word -- a -- after "dispenser comprises" and before "vesicle that comprises".

This certificate supersedes the Certificate of Correction issued June 3, 2008.

Signed and Sealed this

First Day of July, 2008

JON W. DUDAS
*Director of the United States Patent and Trademark Office*